US010792248B2

(12) United States Patent
Tada et al.

(10) Patent No.: US 10,792,248 B2
(45) Date of Patent: Oct. 6, 2020

(54) AQUEOUS SUSPENSION PREPARATION COMPRISING NANOPARTICLES OF MACROLIDE ANTIBACTERIAL AGENT

(71) Applicant: ACTIVUS PHARMA CO., LTD., Funabashi-shi (KR)

(72) Inventors: Takahiro Tada, Funabashi (JP); Kazuhiro Kagami, Funabashi (JP); Shiro Yokota, Funabashi (JP); Kenta Kikuchi, Funabashi (JP)

(73) Assignee: ACTIVUS PHARMA CO., LTD., Funabashi-Shi (JP)

( * ) Notice: Subject to any disclaimer, the term of this patent is extended or adjusted under 35 U.S.C. 154(b) by 0 days.

(21) Appl. No.: 15/034,437

(22) PCT Filed: Nov. 7, 2014

(86) PCT No.: PCT/JP2014/005603
§ 371 (c)(1),
(2) Date: May 4, 2016

(87) PCT Pub. No.: WO2015/068397
PCT Pub. Date: May 14, 2015

(65) Prior Publication Data
US 2016/0271057 A1    Sep. 22, 2016

(30) Foreign Application Priority Data
Nov. 8, 2013 (JP) ................. 2013-231796

(51) Int. Cl.
| | |
|---|---|
| *A61K 9/10* | (2006.01) |
| *A61K 47/32* | (2006.01) |
| *A61K 47/38* | (2006.01) |
| *A61K 31/7048* | (2006.01) |
| *A61K 9/00* | (2006.01) |
| *A61K 9/14* | (2006.01) |
| *A61K 47/10* | (2017.01) |
| *A61K 47/26* | (2006.01) |
| *A61K 31/7052* | (2006.01) |
| *A61K 47/44* | (2017.01) |

(52) U.S. Cl.
CPC ............. *A61K 9/10* (2013.01); *A61K 9/0014* (2013.01); *A61K 9/0019* (2013.01); *A61K 9/0043* (2013.01); *A61K 9/0046* (2013.01); *A61K 9/0048* (2013.01); *A61K 9/14* (2013.01); *A61K 31/7048* (2013.01); *A61K 31/7052* (2013.01); *A61K 47/10* (2013.01); *A61K 47/26* (2013.01); *A61K 47/32* (2013.01); *A61K 47/38* (2013.01); *A61K 47/44* (2013.01)

(58) Field of Classification Search
CPC ...... A61K 9/0048; A61K 9/14; A61K 9/0014; A61K 9/0019; A61K 9/0043; A61K 9/0046; A61K 47/0048; A61K 47/32; A61K 47/38; A61K 47/10; A61K 47/26; A61K 47/44; A61K 31/7048; A61K 31/7052
See application file for complete search history.

(56) References Cited

U.S. PATENT DOCUMENTS

| | | | |
|---|---|---|---|
| 5,085,864 A | 2/1992 | Cannon et al. | |
| 5,098,606 A | 3/1992 | Nakajima et al. | |
| 5,858,410 A | 1/1999 | Muller et al. | |
| 7,056,893 B2 * | 6/2006 | Roy ...................... | A61K 31/02 424/427 |
| 7,205,279 B2 * | 4/2007 | Cottens ................ | A61K 9/1075 424/455 |
| 2006/0205639 A1 * | 9/2006 | Domb ..................... | A61P 11/00 514/20.5 |
| 2007/0015719 A1 * | 1/2007 | Jenkins ................. | A61K 9/145 514/29 |
| 2007/0178152 A1 * | 8/2007 | Shelton .................... | A61K 9/10 424/464 |
| 2008/0160043 A1 * | 7/2008 | Kim ....................... | A61K 36/06 424/195.15 |

(Continued)

FOREIGN PATENT DOCUMENTS

| | | |
|---|---|---|
| CA | 1 297 007 C1 | 3/1992 |
| CN | 10163615 A | 1/2010 |

(Continued)

OTHER PUBLICATIONS

Azhdarzadeh et al., Antibacterial performance of azithromycin nanoparticles as colloidal delivery system against different gram-negative and gram-positive bacteria, Feb. 15, 2012, Advanced Pharmaceutical Bulletin, vol. 2 iss. 1, pp. 17-24.*

Zhang et al., Preparation of Azithromycin Nanosuspensions by High Pressure Homogenization and its Physiochemical Characteristics Studies, 2007, Drug Development and Industrial Pharmacy, vol. 33 iss. 5, pp. 569-575.*

Yutaka Inoue, et al., Application of ascorbic acid 2-glucoside as a solubilizing agent for clarithromycn: Solubilization and nanoparticle formation; International Journal of Pharmaceutics (2007) 331: 38-45.

Joon-Young Hyon, et al., Comparative Efficacy of Topical Gatifloxacin With Ciprofloxacin, Amikacin, and Clarithromycin in the Treatment of Experimental *Mycobacterium chelonae* Keratitis, Arch Ophthalmol (2004) 122: 1166-1169.

(Continued)

*Primary Examiner* — Ali Soroush
(74) *Attorney, Agent, or Firm* — Cowan, Liebowitz & Latman, P.C.; Mark Montague

(57) ABSTRACT

An aqueous suspension preparation that comprises a macrolide antibacterial agent as an active component.
The aqueous suspension preparation is characterized by comprising nanoparticles of a macrolide antibacterial agent and a dispersion stabilizer; an aqueous suspension in which the average particle size of nanoparticles is 500 nm or less and the D90 particle size is 1,500 nm or less; a parenterally administered pharmaceutical composition that comprises this aqueous suspension preparation; an injection preparation; and eye drops or ear drops, more specifically, eye drops for the treatment or prevention of inflammatory diseases of the eye or ear drops for the treatment or prevention of inflammatory diseases of the ear.

19 Claims, 4 Drawing Sheets

(56) References Cited

U.S. PATENT DOCUMENTS

| | | | |
|---|---|---|---|
| 2009/0253807 | A1 | 10/2009 | Sawa et al. |
| 2010/0016597 | A1 | 1/2010 | Hirokawa et al. |
| 2010/0048498 | A1* | 2/2010 | Johnson ............... A61K 9/0095 |
| | | | 514/29 |
| 2013/0216609 | A1 | 8/2013 | Lichter et al. |
| 2013/0237613 | A1* | 9/2013 | Kim ...................... A61K 8/068 |
| | | | 514/777 |

FOREIGN PATENT DOCUMENTS

| | | |
|---|---|---|
| CN | 101636150 | 1/2010 |
| CN | 10420317 B | 2/2017 |
| EP | 2335686 A1 | 6/2011 |
| JP | 3-161430 A | 7/1991 |
| JP | 3-169807 A | 7/1991 |
| JP | 10-508614 | 8/1998 |
| JP | 2001-511780 A | 8/2001 |
| JP | 2007-119456 A | 5/2007 |
| JP | 2010-505965 A | 2/2010 |
| MX | 2014010772 A | 11/2013 |
| RU | 2 025 120 C1 | 12/1994 |
| RU | 2493828 C2 | 9/2013 |
| WO | 90/14094 A1 | 11/1990 |
| WO | 98/33482 A1 | 8/1998 |
| WO | 02/15878 A1 | 2/2002 |
| WO | 2004/006959 A1 | 1/2004 |
| WO | 2004/050021 A2 | 6/2004 |
| WO | 2007/008537 A2 | 1/2007 |
| WO | 2008/127358 A2 | 10/2008 |
| WO | 2010008995 A2 | 1/2010 |
| WO | 2013/168437 A1 | 11/2013 |

OTHER PUBLICATIONS

Robert H. Gross, et al., Corneal Pharmacokinetics of Topical Clarithromycin, Invest Ophthalmol Vis Sci (1995) 36 (5): 965-968.
Jonas, J. Keune, et al., Corneal Pharmacokinetics of Topically Applied Azithromycin and Clarithromycin, Am J Ophthalmol (2004) 138: 547-553.
International Search Report of parent application, PCT/JP2014/005603; dated Jan. 27, 2015; 2 pages; English translation included.
Rashesh K. Kotecha, et al., "Research Artiste Formulation & Process Development of Azithromycin Ophthalmic; Nanosuspension", International Journal of Pharmacy and Pharmaceutical Sciences 2013, pp. 490-497, http://www.jppsournal.com, vol. 4, Issue 4.
A Supplementary European Search Report dated Oct. 13, 2016, which is enclosed, that issued in the corresponding European Patent Application No. 14860926.6
The CN document was cited in a Chinese Office Action dated Feb. 5, 2018, which is enclosed with an English Translation, that issued in Chinese Patent Application No. 201480058606.9.
Taiwanese Office Action dated Jan. 11, 2018, which is enclosed with an English Translation, that issued in Taiwanese Patent Application No. 103138831.
B. Morakul et al., Precipitation-lyophilization-homogenization (PLH) for preparation of clarithromycin nanocrystals: Influencing factors on physicochemical properties and stability, International Journal of Pharmaceutics 457 (2013) 187-196, journal homepage: www.elsevier.com/locate/ijpharm, available online: Sep. 26, 2013.
B. Morakul et al., Dissolution enhancement and in vitro performance of clarithromycin nanocrystals produced by precipitation-lyophilization-homogenization method, European Journal of Pharmaceutics and Biopharmaceutics 88 (2014) 886-896, journal homepage: www.elsevier.com/locate/ejpb, available online: Sep. 6, 2014.
M. Niaz et al., Investigation into physical-chemical variables affecting the manufacture and dissolution of wet-milled clarithromycin nanoparticles, Pharmaceutical Development and Technology, Informa Healtchare, http://informahealthcare.com/phd; ISSN: 1083-7450 (print), 1097-9867 (electronic), Pharm. Dev Technol, 2014: 19 (8):911-921, © 2014 Informa Healthcare USA, Inc. DOI: 10.3109/10837450. 2013.840844, published online: Oct. 4, 2013.
Y. Wang et al., FDA's Regulatory Science Program for Generic PLA/PLGA-Based Drug Products, Posted: Jun. 30, 2017, pp. 1-5, http://www.americanpharmaceuticalreview.com/Featured-Articles/188841-FDA-s-Regulatory-Science-Program-for-Generic-PLA-PLGA-Based-Drug-Products/.
Zhang et al., "Pharmaceutics" Peking University Medical Press, pp. 60-61, 130 Jan. 31, 2005.
The article was cited in a Chinese Office Action dated Aug. 20, 2018, which is enclosed without an English Translation, that issued in Chinese Patent Application No. 15 737 214.5.
Office action dated Nov. 1, 2018 that issued to corresponding Indonesia application No. P00201603779; with English translation.
Chinese Office Action dated Jan. 29, 2019 which is enclosed with a partial English Translation, that issued in Chinese Patent Application No. 201480058606.9. Chinese Office Action dated Aug. 20, 2018 a copy enclosed without English Translation that issued in Chinese Patent Application No. 201480058606.9.
Russian Office Actions dated May 29, 2018 and Nov. 26, 2018, which are enclosed with an English Translation, that both issued in Russian Patent Application No. 2016122544.
Japan Office Action dated Jul. 2, 2018, which is enclosed with an English Translation, that issued in Japan Patent Application No. JP2015-546301.
Israel Office Action dated Sep. 6, 2018, which is enclosed with an English Translation, that issued in Israel Patent Application No. 245406.
Indian Examination Report of the corresponding IN 201627016310 application dated Jan. 15, 2018, which is enclosed with an English Translation.
Chinese Office Action dated Jul. 30, 2019, which is enclosed without an English Translation, that issued in Chinese Patent Application No. 201480058606.9.
European Communication dated Oct. 9, 2019, which is enclosed, that issued in the corresponding European Patent Application No. 14860926.6.
Brazilian Office Action dated Sep. 30, 2019, which is enclosed with an English Translation, that issued in the corresponding Brazil Patent Application No. BR112018010358-0.
Australian Office Action dated Feb. 26, 2019, which is enclosed; that issued in Australian Application No. 2014345193.
Mexican Office Action dated May 7, 2019, which is enclosed with an English translation, that issued in the corresponding Mexican Patent Application No. MX/a/2016/005764.
"Bolshoi solver meditsinskikh terminov, Fedotov V.D, M: ZAO tsentrpoligraf", (2007) (2 pages).
The above reference was cited in an Mexican Office Action dated Oct. 9, 2018, which is enclosed, that issued in the corresponding Mexican Application No. MX/a/2016/005764, with English translation.
Office Action of the corresponding RU 2493828 application; dated Sep. 26, 2018, which is enclosed with an English Translation.

* cited by examiner

[Figure 1]
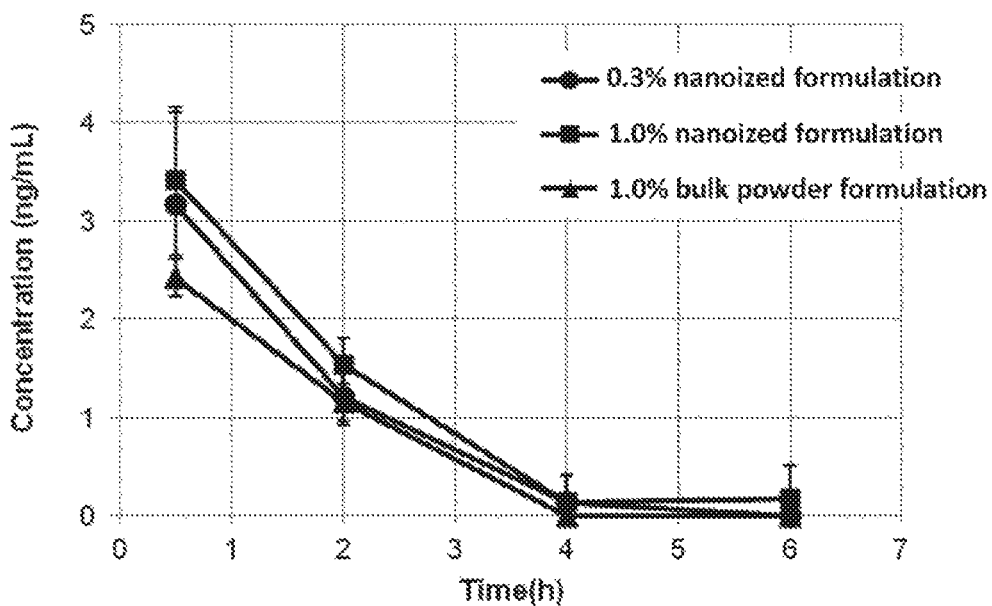
[Figure 2]
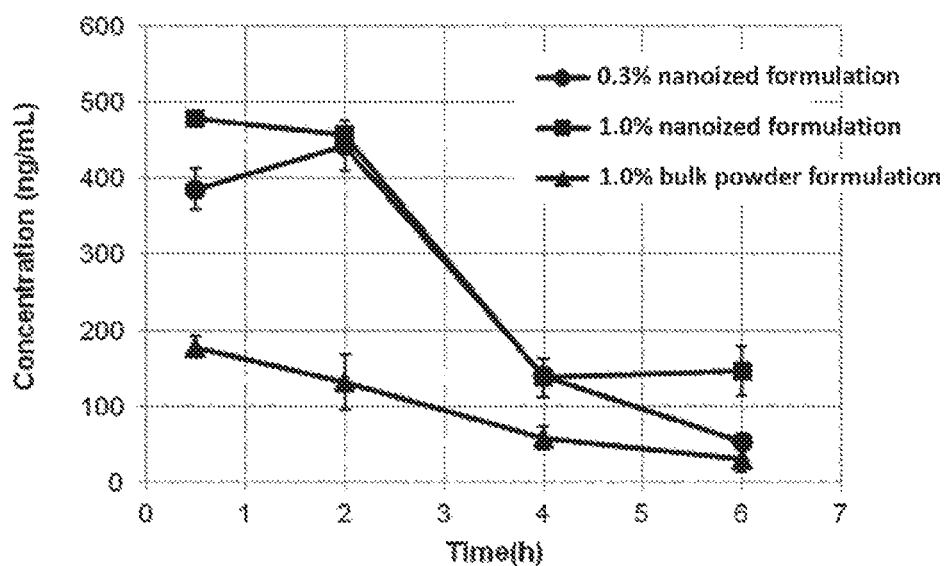

[Figure 3]
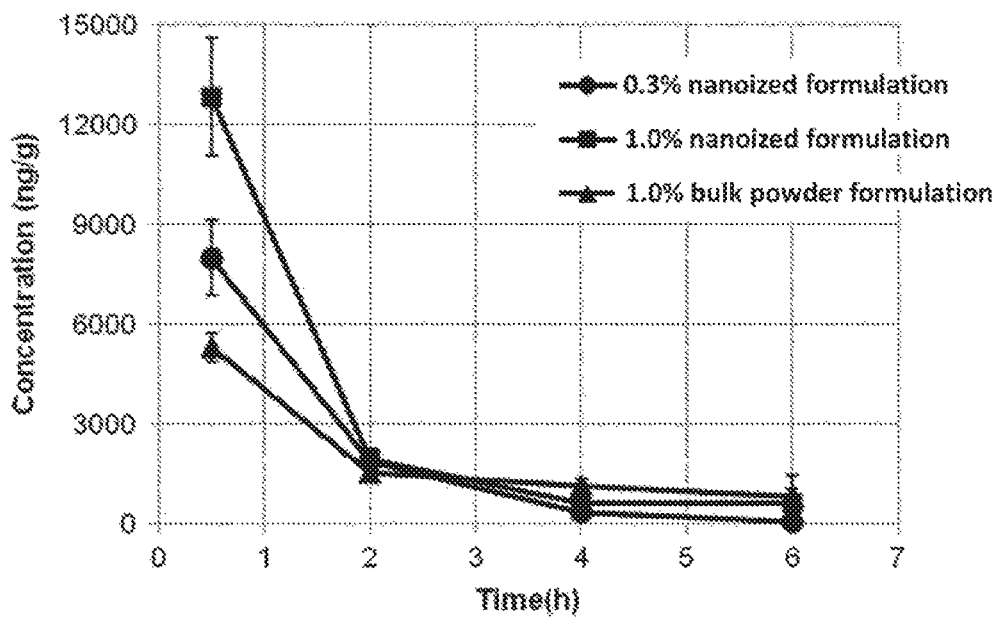
[Figure 4]
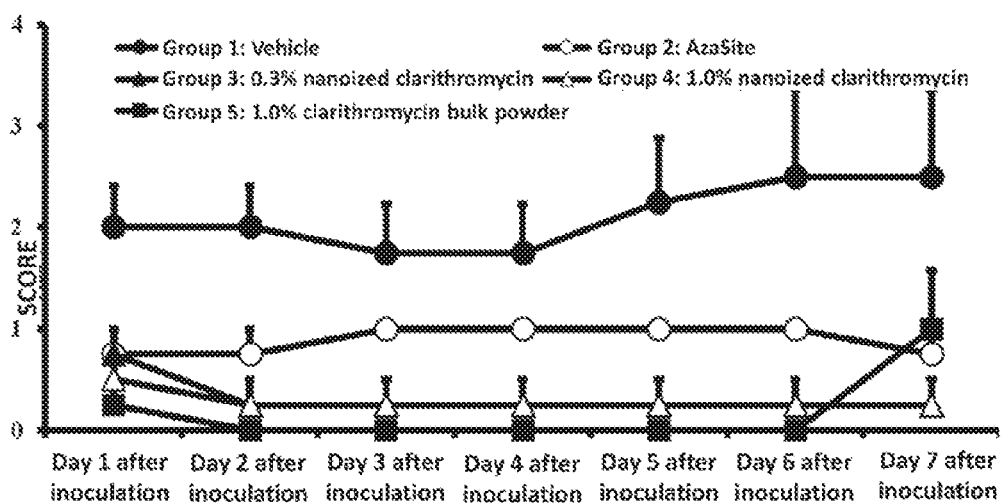

[Figure 5]
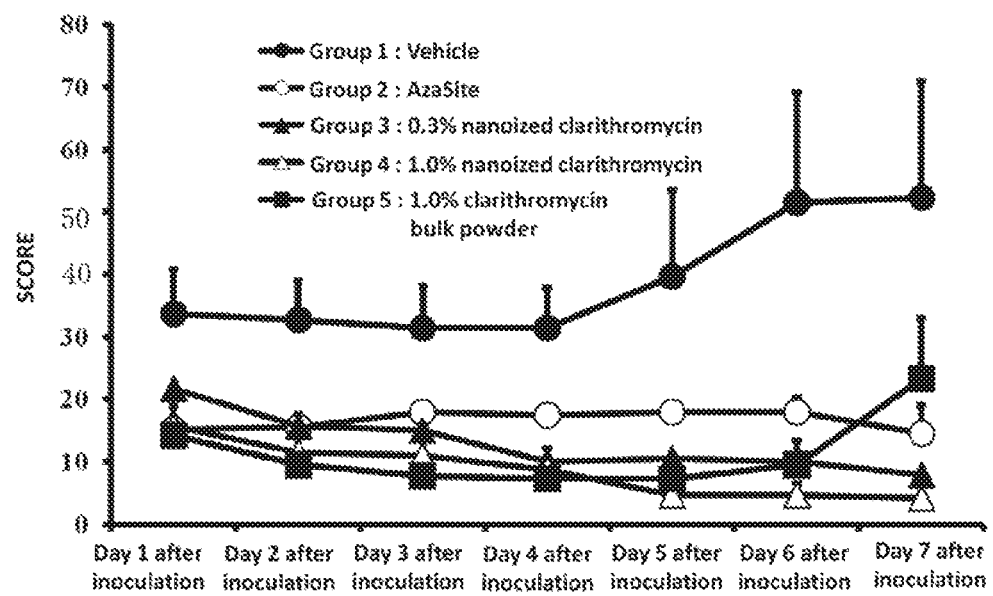
[Figure 6]
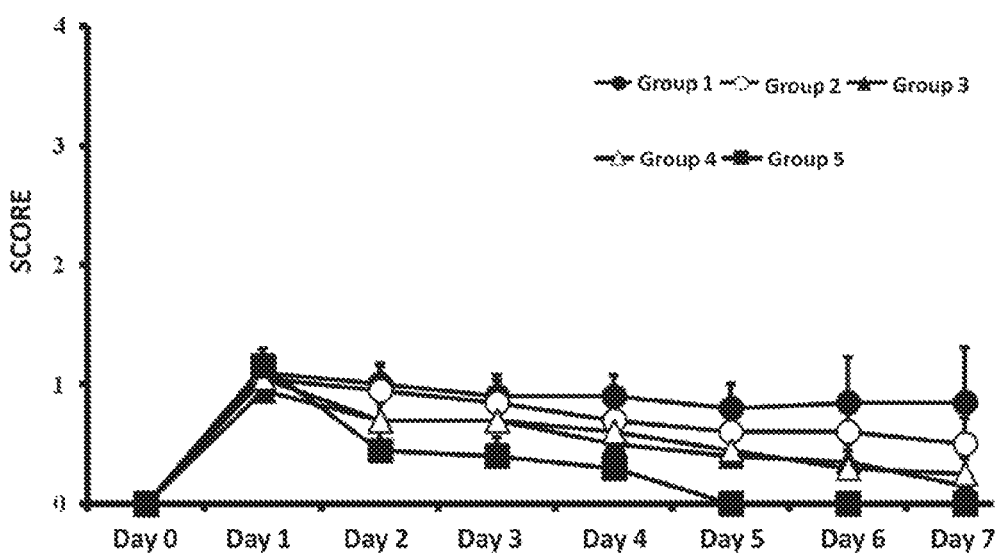

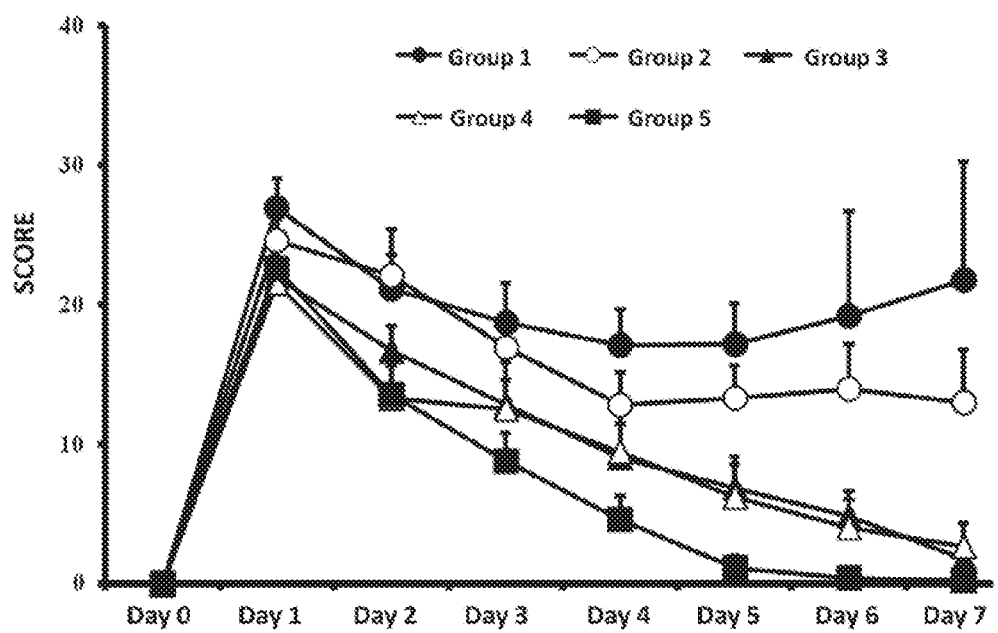
[Figure 7]

AQUEOUS SUSPENSION PREPARATION COMPRISING NANOPARTICLES OF MACROLIDE ANTIBACTERIAL AGENT

CROSS REFERENCE TO RELATED APPLICATIONS

This is a U.S. national phase of application No. PCT/JP2014/005603, filed on Nov. 7, 2014. This application claims the priority to the Japanese Patent Application No. 2013-231796, filed on Nov. 8, 2013, and the disclosures of all of which are herein incorporated by reference in their entirety. All of the contents disclosed in the cited patents, patent applications, and literatures are herein incorporated by reference in their entirety.

TECHNICAL FIELD

The present invention relates to an aqueous suspension formulation comprising nanoparticles of a macrolide antibiotic and a use thereof.

BACKGROUND ART

Macrolide antibiotics such as erythromycin, roxithromycin, clarithromycin, and azithromycin have been mainly used via oral administration, and there is a demand of macrolide antibiotics in topical formulations such as injections, eye drops, or ear drops. However, these drugs are poorly soluble compounds having a low solubility, which makes it difficult to formulate them into liquid formulations. Of these, erythromycin is easily soluble in methanol, ethanol, and acetone, and slightly soluble in ether, but extremely hardly soluble in water. Clarithromycin, while being slightly soluble in acetone and chloroform, is very slightly soluble in methanol, ethanol, and ether, and practically insoluble in water. Thus, clarithromycin is recognized to be not only practically insoluble in water but also hardly soluble in an organic solvent used for biological experiments as compared with erythromycin, and thus significantly difficult to be formulated into a solution. As a formulation of such poorly soluble drugs in topical formulations such as injections, eye drops, or ear drops, an aqueous suspension formulation in which such a poorly soluble drug is suspended is known. For example, an aqueous suspension formulation for topical administration is reported, which contains nanoparticles (the diameter of 90% or more of the fine particles of a poorly soluble drug are less than 1000 nm) of the poorly soluble drug and a granule disintegrator (Patent Literature 1). It is also reported that aqueous suspension formulations such as eye drops and ear drops comprising a poorly soluble drug, polyvinylpyrrolidone, and alginic acid or a salt thereof have good redispersibility (Patent Literature 2).

Poorly soluble drugs are also known to have poor oral bioavailability. In order to improve the oral bioavailability, various studies to solubilize and suspense the poorly soluble drugs have been conducted. For example, it is reported that clarithromycin have an enhanced solubility, when pulverized with L-ascorbic-acid 2-glycoside (Non Patent Literature 1). It is further reported that a liquid administration composition of nanoparticles is formulated with an (poorly soluble) active substance particle having an effective average diameter of less than 2000 nm and with a surface stabilizer and an osmotically active crystal growth inhibitor, which is stabilized and prevented dissolution/recrystallization and aggregation of the active substance (Patent Literature 3). It is also reported that the formulation of clarithromycin having an effective average diameter of less than 2000 nm combined with a surface stabilizer showed a higher solubility and higher oral bioavailability (Patent Literature 4).

Various studies have also been reported on parenteral administration forms such as injections of poorly soluble drugs such as clarithromycin. For example, an administration of poorly soluble drugs such as clarithromycin by injection has problem of a pain at an injected site. As solutions of this problem, a method for formulating a lipid emulsion (Patent Literature 5), a method for embedding a poorly soluble drug into a liposome (Patent Literature 6), and a method for encapsulating a poorly soluble drug in micelles of a bile salt (Patent Literature 7) have been reported.

On the other hand, a topical administration of macrolide antibiotics have been reported to be effective on keratitis, particularly on post-LASIK keratitis caused by nontuberculous mycobacteria (Non Patent Literature 2). Especially, clarithromycin has demonstrated to be suitable for treating keratitis caused by nontuberculous mycobacteria by animal experiments. The clarithromycin is reported to be four to eight times as effective as azithromycin against nontuberculous mycobacteria. It has been attempted to formulate these drugs in formulations for topical administration such as an eye drop and an ear drop, and the DuraSite (registered trademark) technique for formulation has been enabled a practically use of an Azithromycin eye drop. However, clarithromycin has not been practically used in an eye drop form yet. Regarding to clarithromycin ocular instillation, it has been disclosed that a clarithromycin powder was dissolved in methanol and then diluted with saline, which was instilled into a rabbit eye, and that the administered clarithromycin was retained in the cornea of the rabbit (Non Patent Literature 3). Conversely, it is also reported that clarithromycin was not detected in the cornea but rather causes inflammation on the ocular surface after administration of a clarithromycin suspension in the same manner. In this report, the clarithromycin suspension was prepared by suspending a clarithromycin granule for oral administration in a sterilized water and then diluting the suspension with saline (Non Patent Literature 4). It is reported that 1 to 2% of the patients experienced such an irritation in the clinical trial on azithromycin eye drops.

For the ear drops, ear drops comprising a macrolide antibiotic such as clarithromycin or azithromycin as an effective ingredient have not been practically used yet, despite the reports made on an ear drop formulation for long lasting administration (Patent Literature 8) and a formulation for a macrolide antibiotic to topically stay on the eardrum for an extended period of time (Patent Literature 9).

CITATION LIST

Patent Literature

Patent Literature 1: Japanese Patent Laid-Open No. 2007-119456
Patent Literature 2: International Publication No. WO 2002/015878
Patent Literature 3: International Publication No. WO 2004/006959
Patent Literature 4: International Publication No. WO 2007/008537
Patent Literature 5: International Publication No. WO 90/14094

Patent Literature 6: International Publication No. WO 98/33482
Patent Literature 7: Japanese Patent Laid-Open No. H3-169807
Patent Literature 8: U.S. Unexamined Patent Application Publication No. 2013/0216609
Patent Literature 9: International Publication No. WO 2004/050021

Non Patent Literature

Non Patent Literature 1: Yutaka Inoue et al., International Journal of Pharmaceutics (2007) 331:38-45
Non Patent Literature 2: Joon-Young Hyon et al., Arch Ophthalmol (2004) 122:1166-1169
Non Patent Literature 3: Robert H. Gross et al., Invest Ophthalmol Vis Sci (1995) 36(5):965-968
Non Patent Literature 4: Jonas, J. Kuehne et al., Am J Ophthalmol (2004) 138:547-553

SUMMARY OF INVENTION

Technical Problem

Despite various studies on aqueous liquid formulations comprising a poorly soluble drug, it has still been difficult to achieve practically usable aqueous suspension formulations such as injections, eye drops, and ear drops comprising a poorly soluble drug such as clarithromycin. Therefore, injections and aqueous suspension formulations for topical administration, particularly eye drops and ear drops are desired to be developed, which are preferably less irritable, easily sterilizable, have good temporal stability and dispersion stability, and are applicable to a wide range of poorly soluble drugs.

Accordingly, the present invention is objected to provide an aqueous suspension comprising the macrolide antibiotic as an effective ingredient, which is less irritable, easily sterilizable, and has good temporal stability and dispersion stability. Specifically, the present invention is objected to provide an practically feasible aqueous pharmaceutical composition, such as an injection, an eye drop, an ear drop, a nose drop, and/or an inhaler, comprising a macrolide antibiotic as an effective ingredient. Particularly, the present invention is objected to provide an injection, an eye drop, an ear drop, a nose drop, and/or an inhaler comprising a macrolide antibiotic as an effective ingredient which has good clarity, (long term) dispersibility, preservation stability, cornea retainability, aqueous humor migration properties, and low irritability. The present invention is further objected to provide the above aqueous suspension or an injection, an eye drop, an ear drop, a nose drop, and/or an inhaler comprising clarithromycin as the macrolide antibiotic as an effective ingredient.

Solution to Problem

The present inventors conducted extensive studies and consequently have found that an aqueous suspension formulation comprising nanoparticles of a macrolide antibiotic, and a dispersion stabilizer, a surfactant, an aggregation inhibitor, and/or a viscosity modifier has good clarity, (long term) dispersibility, preservation stability, cornea retainability, and aqueous humor migration properties, and is thus good to be an aqueous pharmaceutical composition. Particularly, the present inventors have found that extremely advantageous effects are exerted when the nanoparticles of a macrolide antibiotic has an average particle diameter (hereinafter referred to as "Dv") of 500 nm or less and a 90% diameter (hereinafter referred to as "D90") of 1500 nm or less (preferably a Dv is 300 nm or less and a D90 is 400 nm or less, or a Dv is 200 nm or less and a D90 is 300 nm or less).

In one embodiment, the present invention relates to an aqueous suspension formulation comprising the nanoparticles of a macrolide antibiotic, and preferably relates to the aqueous suspension formulation wherein the nanoparticle has a Dv of 500 nm or less and a D90 of 1500 nm or less. For example, the aqueous suspension formulation of the present invention includes the nanoparticles of a macrolide antibiotic produced by mixing the macrolide antibiotic, a physiologically acceptable salt and/or a physiologically acceptable saccharide, a physiologically acceptable polyol and/or water, and a dispersion stabilizer.

The present inventors further have found that the above aqueous suspension formulation can be suitable for use as the aqueous pharmaceutical composition by using a surfactant of polyoxyethylene hydrogenated castor oil and/or a thickener of hydroxypropyl methyl cellulose or methyl cellulose as the dispersion stabilizers. The present inventors particularly have found that the ocular topical formulation of a macrolide antibiotic comprising a polyoxyethylene hydrogenated castor oil (HCO-60 (surfactant)) and hydroxypropyl methyl cellulose (HPMC (polymer thickener)) or methyl cellulose (MC (polymer thickener)) as a dispersion stabilizer is advantageous in following points: an interaction with mucous membranes of cornea and conjunctiva can be expected due to polymer compounds HPMC and MC; a cornea retainability can be expected due to the effect of HPMC or MC and due to stability of nanoparticles in the formulation; and the aqueous humor migration properties can be enhanced due to the extended retention time.

Further, the present inventors have found that the solubility of the macrolide antibiotics can be enhanced by employing the nanoparticle in the formulation, and thereby a dosage amount can be reduced. Also, the present inventors have unexpectedly found that the problem of irritation caused by the macrolide antibiotics is reduced by the employment of the nanoparticle or the nanoparticle formulation of the present invention. With these findings, the inventors accomplished the present invention.

In one embodiment, the present invention relates to the aqueous suspension formulation comprising the nanoparticles (preferably the nanoparticle has a Dv of 500 nm or less and a D90 of 1500 nm or less) of a macrolide antibiotic. For example, the present invention encompasses the aqueous suspension formulation comprising the nanoparticles (preferably the nanoparticle has a Dv of 500 nm or less and a D90 of 1500 nm or less) of a macrolide antibiotic and a dispersion stabilizer. The present invention also relates to the aqueous suspension formulation wherein the dispersion stabilizer is a surfactant(s), an aggregation inhibitor(s), and/or a viscosity modifier(s). In a preferable embodiment of the present invention, the surfactant is polyoxyethylene hydrogenated castor oil 60, polysorbate 80, polyethylene glycol monostearate, and/or polyoxyethylene polyoxypropylene glycol, and/or the aggregation inhibitor is polyvinyl alcohol, polyethylene glycol, and/or polyvinylpyrrolidone, and/or the viscosity modifier is methyl cellulose, hydroxypropyl methyl cellulose, and/or hydroxyethyl cellulose. For example, the present invention may be the aqueous suspension comprising the nanoparticles of a maclolide antibacterial drug, which comprises HCO-60 (surfactant), and HPMC or MC (polymer thickener) as the dispersion stabilizers.

In another embodiment, the present invention relates to the aqueous pharmaceutical composition comprising the nanoparticles of a macrolide antibiotic, which optionally comprises a dispersion stabilizer. In this specification, an aqueous pharmaceutical composition means an aqueous liquid or gelatinous pharmaceutical composition, and specifically means a pharmaceutical composition in which the nanoparticles of a macrolide antibiotic are suspended in an aqueous liquid. Thus, the pharmaceutical composition used herein means an aqueous pharmaceutical composition unless otherwise stated. The aqueous pharmaceutical composition includes injections and topical formulations. The topical formulation used herein means an aqueous formulation for topical administrations unless otherwise stated.

Specifically, the injection of the present invention may be an injection for treating or preventing a systemic or topical inflammatory disease or a systemic or topical infectious disease, and includes intravenous injections, subcutaneous injections, intramuscular injections, intravenous drips, and the like. The topical formulation includes an ocular topical formulation, an otic topical formulation, a nasal topical formulation, and a pulmonary topical formulation. More specifically, the topical formulation includes a pharmaceutical composition for treating or preventing inflammatory diseases or infectious diseases of eye, ear, nose, or lung. For example, the topical formulation includes eye drops, ear drops, nose drops, and inhalers. The topical formulation of the present invention may preferably be a ocular topical formulation for treating or preventing ocular inflammatory diseases or ocular infectious diseases, a otic topical formulation for treating or preventing otogenic inflammatory diseases or otogenic infectious diseases, a nasal topical formulation for treating or preventing nasal inflammatory diseases or nasal infectious diseases, or a pulmonary topical formulation for treating or preventing pulmonary inflammatory diseases or pulmonary infectious diseases.

The aqueous pharmaceutical composition of the present invention can be used to treat or prevent an inflammatory disease or infectious disease by topically administering an effective dose of the composition to a patient in need thereof. In one embodiment, the present invention relates to a method for treatment or prevention of inflammatory diseases or infectious diseases, comprising administering an effective dose of the aqueous suspension formulation to a patient in need thereof, wherein the aqueous suspension formulation comprises the nanoparticles of a macrolide antibiotic and optionally a dispersion stabilizer, or an effective dose of the pharmaceutical composition comprising such an aqueous suspension formulation. For example, the present invention encompasses a method for treatment or prevention of inflammatory diseases or infectious diseases comprising topically administering an effective dose of the topical formulation to a patient in need thereof, wherein the topical formulation comprises the nanoparticles of a macrolide antibiotic and optionally a dispersion stabilizer.

Alternatively, the present invention relates to a use of the nanoparticles of a macrolide antibiotic (and optionally a dispersion stabilizer) for producing aqueous pharmaceutical compositions (e.g., injections and topical formulations). The present invention also includes a use of the aqueous suspension formulation comprising the nanoparticles (preferably the nanoparticle has a Dv of 500 nm or less and a D90 of 1500 nm or less) of a macrolide antibiotic (and optionally a dispersion stabilizer) for producing aqueous pharmaceutical compositions (e.g., injections and topical formulations).

The "macrolide antibiotic" used herein is not particularly limited as long as it is a compound having the macrolide skeleton and an antibacterial activity. The macrolide skeleton may be a 14 to 16-membered ring macrolide, preferably a 14-membered ring macrolide. The macrolide antibiotic can include, for example, erythromycin, clarithromycin, roxithromycin, azithromycin, josamycin, rokitamycin, and kitasamycin, preferably is erythromycin, clarithromycin, and azithromycin, and most preferably is clarithromycin.

The "aqueous suspension formulation" used herein means an aqueous liquid formulation in which the nanoparticles of a macrolide antibiotic are suspended, and is preferably an aqueous suspension formulation for medical use. The aqueous suspension formulation and the pharmaceutical composition herein may have viscosity as long as it does not prevent to be used as a pharmaceutical drug, and can include gelatinous formulations as well as the liquid formulations. The aqueous suspension formulation and the pharmaceutical composition herein include the injections and topical formulations. The "topical" used herein means a part of the body, such as affected areas, an area around an affected area, or an organ of an affected area, and preferably eye, ear, nose (upper respiratory tract), and lung (lower respiratory tract). The "topical formulation" means a pharmaceutical composition for the purpose of a topical administration. The topical formulations are preferably ocular topical formulations (e.g., eye drops), otic topical formulations (e.g., ear drops), nasal topical formulations (e.g., nose drops), and pulmonary topical formulations (e.g., inhalers). The aqueous suspension formulation herein itself can constitute a pharmaceutical composition administerable as a pharmaceutical product, or alternatively the aqueous suspension formulation may be a component which provides an administerable pharmaceutical composition (e.g., raw ingredient for a pharmaceutical composition) by being added other components and/or a diluent.

The aqueous suspension formulation herein exhibits any one, or two or more, of the following properties: (1) no precipitation is observed by a naked eye, (2) a clarity is high, and (3) no aggregate or crystal is microscopically detected, preferably 24 hours (preferably 2 days, 3 days, 4 days, 5 days, 6 days, or 7 days) after dispersion by stirring or the like (at room temperature). The aqueous suspension formulation comprising the nanoparticles of a macrolide antibiotic herein is preferably that no precipitate is observed with a naked eye, a high clarity, and no aggregate or crystal detected microscopically after 7 days from sealed in a test tube.

The clarity is determined in accordance with the clarity test described in the Japanese Pharmacopoeia. Specifically, the clarity can be determined by the following procedure: a comparison solution for turbidity is prepared by adding water to 5 mL of a formazin standard emulsion to total volume of 100 mL. A test aqueous suspension formulation and a newly prepared comparison solution for turbidity are poured into a flat-bottom colorless clear glass test tube having an inner diameter of 15 mm until the solution layer reaches a depth of 30 mm or 40 mm, respectively, which are observed and compared from above on a black color background in the scattering light. When the clarity of the test aqueous suspension formulation is the same as water or the solvent used, or when the degree of turbidity of the test aqueous suspension formulation is the same or less than the turbidity of the comparison solution, the clarity is determined to be high. Alternatively, the test aqueous suspension formulation and the newly prepared comparison solution for turbidity can be tested for clarity by the ultraviolet visible spectrophotometry method wherein a transmittance at 660 nm is measured using a cell having a layer length of 50 mm and using water or the solvent as the control. When the transmittance of the test aqueous suspension formulation is equal to or higher than that of the comparison solution for turbidity, the clarity can be determined to be high.

In another embodiment, the topical formulation of the present invention is an ocular topical formulation having a high cornea retentability. The cornea retentability of a test aqueous suspension formulation can be tested in accordance with, for example, the method described in Jonas, J. Kuehne et al., Am J Ophthalmol (2004) 138:547-553. Specifically, the test aqueous suspension of a drug can be administered to an eye of a rabbit, and a concentration of the drug in a cornea is measured. When the drug concentration in the cornea is higher than that measured for administration of standard solution (e.g., the formulation reported to have been tested as a ocular topical formulation, for example, for clarithromycin, a sterilized water suspension of the clarithromycin granule for oral administration (see Jonas, J. Kuehne et al., Am J Ophthalmol (2004) 138:547-553), the same applies hereinafter), the cornea retainability of the test aqueous suspension can be determined to be high.

In an embodiment, the aqueous suspension formulation of the present invention is an aqueous suspension formulation with a low irritability. The low irritability used herein means that the degree of irritation reaction (for example, inflammation reactions such as flare, swelling, and/or congestion) in administering to a subject is less than the irritation reaction caused by an administration of the previously used aqueous formulation comprising the same effective drugs. The degree of irritation of the test aqueous suspension formulation can be determined, for example in accordance with the method described in Jonas, J. Kuehne et al., Am J Ophthalmol (2004) 138:547-553, by administering the test aqueous suspension formulation to an eye of a rabbit and measuring the degree of inflammation in the eye. When the degree of inflammation is lower than the standard solution (same as above), the irritability of test aqueous suspension formulation is determined to be low. More specifically, the irritability of an eye drop can be determined by applying a formulation of a macrolide antibiotic at a concentration of 1.0% to an eye once to 20 times a day at an interval of 30 minutes to several hours, observing a cornea, an iris, and conjunctiva at the following timing: before administration, and 1, 3, 5, and 24 hours after the final administration, and scoring the results in accordance with the Draize's evaluation criteria (see OECD GUIDELINES FOR TESTING OF CHEMICALS 405 (24 Feb. 1987) Acute Eye Irritation/Corrosion).

The "surfactant" used herein is not particularly limited as long as it can be administered to human as a pharmaceutical additive without toxicity and does not prevent the activity of macrolide antibiotics. Examples can include (i) nonionic surfactants such as polyoxyethylene (hereinafter referred to as "POE")-polyoxypropylene (hereinafter referred to as "POP") block copolymers such as poloxamer 407, poloxamer 235, and poloxamer 188; polyoxyethylene-polyoxypropylene block copolymer adducts of ethylenediamine such as poloxamine; POE sorbitan fatty acid esters such as POE (20) sorbitan monolaurate (polysorbate 20), POE (20) sorbitan monooleate (polysorbate 80), and polysorbate 60; POE hydrogenated castor oils such as POE (60) hydrogenated castor oil; POE alkyl ethers such as POE (9) lauryl ether; POE/POP alkyl ethers such as POE (20) POP (4) cetyl ether; POE alkylphenyl ethers such as POE (10) nonyl phenyl ether; POE/POP glycols such as POE (105) POP (5) glycol, POE (120) POP (40) glycol, POE (160) POP (30) glycol, POE (20) POP (20) glycol, POE (200) POP glycol (70), POE (3) POP (17) glycol, POE (42) POP (67) glycol, POE (54) POP (39) glycol, and POE (196) POP (67) glycol; (ii) amphoteric surfactants such as glycine amphoteric surfactants such as alkyldiaminoethyl glycine, betaine acetate amphoteric surfactants such as lauryl dimethylaminoacetic acid betaine, and imidazoline amphoteric surfactants; (iii) anionic surfactants such as POE alkyl ether phosphates and salts thereof such as POE (10) sodium lauryl ether phosphate; N-acylamino acid salts such as sodium lauroyl methyl alanine; alkyl ether carboxylate; N-acyl taurine salts such as sodium N-coconut acid N-methyl taurate; sulfonates such as sodium C14-16 olefin sulfonate; alkyl sulfates such as sodium lauryl sulfate; POE alkyl ether sulfates such as sodium POE (3) lauryl ether sulfate; and α-olefin sulfonate; (iv) cationic surfactants such as alkylamine salts; alkyl quarternary ammonium salts such as benzalkonium chloride, benzethonium chloride; and alkyl pyridinium salts such as cetylpyridinium chloride, cetylpyridinium bromide. The aqueous suspension formulation of the present invention may contain one, or two or more, of the surfactants. The surfactant are preferably polyoxyethylene hydrogenated castor oil 60 (HCO-60), polysorbate 80 (Tween 80), polyethylene glycol monostearate (MYS-40), and/or polyoxyethylene polyoxypropylene glycol.

The "aggregation inhibitor" used herein is not particularly limited as long as it can inhibit the aggregation of a macrolide antibiotic, can be administered to human without toxicity, and does not prevent an activity of the macrolide antibiotic. Examples include alkyl sulfate; N-alkyloyl methyl taurine salt; ethanol; glycerol; propylene glycol; sodium citrate; phospholipids such as glycerophospholipid (lecithin (phosphatidylcholine) (e.g., purified soybean lecithin, hydrogenated soybean lecithin), phosphatidylserine, phosphatidylethanolamine, phosphatidylinositol, phosphatidic acid, phosphatidylglycerol, lysophosphatidylcholine, lysophosphatidylserine, lysophosphatidylethanolamine, lysophosphatidylinositol, lysophosphatidic acid, and lysophosphatidylglycerol), and sphingophospholipid (sphingomyelin, ceramide, glycosphingolipid, or ganglioside); D-sorbitol; lactose; xylitol; gum arabic; sucrose fatty acid ester; polyoxyethylene hydrogenated castor oil; polyoxyethylene fatty acid esters; polyethylene glycol (PEG); polyoxyethylene sorbitan fatty acid ester; alkyl benzene sulfonate; sulfosuccinate; polyoxyethylene polyoxypropylene glycol; polyvinylpyrrolidone (PVP); polyvinyl alcohol (PVA); hydroxypropyl cellulose (HPC); methyl cellulose (MC); hydroxyethyl cellulose (HEC); hydroxypropyl methyl cellulose (HPMC); carmellose sodium; carboxyvinyl polymer (CVP); N-acyl-glutamate; acrylic acid copolymer; methacrylic acid copolymer; casein sodium; L-valine; L-leucine; L-isoleucine; benzalkonium chloride; and benzethonium chloride. The aqueous suspension formulation of the present invention may contain one, or two or more, of the aggregation inhibitors. Preferable aggregation inhibitors are polyvinyl alcohol (PVA), polyethylene glycol (PEG), and/or polyvinylpyrrolidone (PVP).

The "viscosity modifier" used herein is not particularly limited as long as it can modify the viscosity of an aqueous suspension formulation, can be administered to human as a pharmaceutical additive without toxicity, and does not prevent an activity of a macrolide antibiotic. Examples can include polysaccharides or derivatives thereof (gum arabic, gum karaya, xanthan gum, carob gum, guar gum, gum guaiac, quince seed, darman gum, gum tragacanth, benzoin rubber, locust bean gum, casein, agar, alginic acid, dextrin, dextran, carrageenan, gelatin, collagen, pectin, starch, polygalacturonic acid, chitin and derivatives thereof, chitosan and derivatives thereof, elastin, heparin, heparinoid, heparin sulfate, heparan sulfate, hyaluronic acid, chondroitin sulfate, and the like), ceramide, cellulose derivatives (methyl cellulose, ethyl cellulose, hydroxyethyl cellulose, hydroxypropyl cellulose, hydroxypropyl methyl cellulose, carboxymethyl cellulose, carboxyethyl cellulose, cellulose, cellulose nitrate, and the like), polyvinyl alcohol (completely or partially saponified), polyvinylpyrrolidone, Macrogol, polyvinyl methacrylate, polyacrylic acid, carboxyvinyl polymer, polyethyleneimine, polyethylene oxide, polyethylene glycol, ribonucleic acid, deoxyribonucleic acid, methyl vinyl ether-maleic anhydride copolymer, and pharmacologically acceptable salts thereof (e.g., sodium alginate). The aqueous suspension formulation of the present invention may contain one, or two or more, of the viscosity modifiers. Preferable viscosity modifiers are methyl cellulose (MC), hydroxypropyl methyl cellulose (HPMC), and/or hydroxyethyl cellulose (HEC).

The dispersion stabilizer used herein is preferably a surfactant and/or a thickener, more preferably polyoxyethylene hydrogenated castor oil, hydroxypropyl methyl cellulose, and/or methyl cellulose, and may be polyoxyethylene hydrogenated castor oil and hydroxypropyl methyl cellulose, or polyoxyethylene hydrogenated castor oil and methyl cellulose.

Herein, the surfactant, aggregation inhibitor, and/or viscosity modifier (hereinafter, referred to as "agent" in this paragraph) which can be also used as the dispersion stabilizer may adhere to or can be adsorbed on the surface of nanoparticles of macrolide antibiotic. These agents added before pulverization step can adhere to or being adsorbed on the surface of nanoparticles of macrolide antibiotic, thereby preventing nanoparticles from aggregation during the pulverization step. Additionally, the adherence and the absorbance of these agents on the surface of nanoparticles of macrolide antibiotic have an effect of prevention of aggregation in the aqueous suspension formulation. In this specification, the adherence and the absorbance of surfactant, aggregation inhibitor, and/or viscosity modifier used as a dispersion stabilizer on the surface of nanoparticles of the macrolide antibiotic means that at least a part of these agents adheres to or is adsorbed on the nanoparticles surface (contributing to the surface modification), but does not mean no existence of these agents without adhering or being adsorbed to the surface in the aqueous suspension formulation. In other words, the surfactant, aggregation inhibitor and/or viscosity modifier used as the dispersion stabilizer can modify the surface of nanoparticles of the macrolide antibiotic and thus can be regarded as "surface modifier" of the macrolide antibiotic.

The macrolide antibiotic contained in the aqueous suspension formulation of the present invention is in the form of nanoparticle. The average particle diameter (Dv) of the macrolide antibiotic is 500 nm or less, preferably 400 nm or less, 300 nm or less, 200 nm or less, 150 nm or less, and most preferably 145 nm or less. For example, the average particle diameter range of the macrolide antibiotic may be 20 to 500 nm, 20 to 400 nm, 20 to 300 nm, and 20 to 200 nm, preferably 50 to 400 nm, 50 to 300 nm, 50 to 200 nm, and 50 to 150 nm. The 90% diameter (D90) of the macrolide antibiotic is 1500 nm or less, preferably 1200 nm or less, 1000 nm or less, 800 nm or less, 700 nm or less, 600 nm or less, 500 nm or less, 400 nm or less, 300 nm or less, 200 nm or less, and most preferably 197 nm or less. For example, the 90% diameter (D90) range of the macrolide antibiotic may be 50 to 1200 nm, 50 to 1000 nm, 50 to 800 nm, and 50 to 700 nm, preferably 80 to 800 nm, 80 to 700 nm, 80 to 600 nm, 80 to 500 nm, and further preferably 100 to 600 nm, 100 to 500 nm, 100 to 400 nm, and 100 to 300 nm. Since macrolide antibiotic, the effective ingredient, is in the form of nanoparticles in the aqueous suspension formulation, the formulation can be sterilized by a filter, which can enable easy sterilization without affecting the physicochemical properties of the active ingredient.

The nanoparticle of a macrolide antibiotic contained in the aqueous suspension formulation of the present invention is preferably nanoparticles produced by mixing the macrolide antibiotic, a physiologically acceptable salt and/or a physiologically acceptable saccharide, a physiologically acceptable polyol and/or water, and a dispersion stabilizer. The nanoparticle of a macrolide antibiotic of the present invention is more preferably those produced by mixing the macrolide antibiotic, a physiologically acceptable salt and/or a physiologically acceptable saccharide, a physiologically acceptable polyol and/or water, and a dispersion stabilizer, and by added lecithin during or after pulverization.

Advantageous Effects of Invention

The aqueous suspension formulation comprising the nanoparticles of a macrolide antibiotic (and a dispersion stabilizer) of the present invention has good clarity, (long term) dispersibility, preservation stability, cornea retainability, and aqueous humor migration properties, low irritability, easy sterilizability, good temporal stability and dispersion stability, and thus can be used as a pharmaceutical composition for parenteral administration.

BRIEF DESCRIPTION OF DRAWINGS

FIG. 1 is a graph showing over-time changes of the clarithromycin concentration in the plasma. In the figure, the ordinate refers to a clarithromycin concentration (ng/mL) in the plasma, and the abscissa refers to elapsed time (h). In the figure, the circle denotes a 0.3% nanoized formulation, the square denotes a 1% nanoized formulation, and the triangle denotes a 1% bulk powder formulation.

FIG. 2 is a graph showing over-time changes of the clarithromycin concentration in the aqueous humor. In the figure, the ordinate refers to a clarithromycin concentration (ng/mL) in the aqueous humor, and the abscissa refers to elapsed time (h). In the figure, the circle denotes a 0.3% nanoized formulation, the square denotes a 1% nanoized formulation, and the triangle denotes a 1% bulk powder formulation.

FIG. 3 is a graph showing over-time changes of the clarithromycin concentration in the conjunctiva. In the figure, the ordinate refers to a clarithromycin concentration (ng/mL) in the conjunctiva, and the abscissa refers to elapsed time (h). In the figure, the circle denotes a 0.3% nanoized formulation, the square denotes a 1% nanoized formulation, and the triangle denotes a 1% bulk powder formulation.

FIG. 4 is a graph showing the results of drug efficacy test in accordance with evaluation criteria of Hatano et al. and Nakamura et al. The ordinate refers to the score, and the abscissa refers to the number of days passed since the inoculation of a bacterium liquid. The black circle denotes the control group (vehicle), the white circle denotes AzaSite administered group, the black triangle denotes the 0.3% nanoized clarithromycin formulation administered group, the white triangle denotes the 1% nanoized clarithromycin formulation administered group, and the black square denotes the 1% clarithromycin bulk powder formulation administered group. The value refers to average values, and the error bar refers to the standard deviation.

FIG. 5 is a graph showing the results of drug efficacy test in accordance with evaluation criteria of Draize et al. The ordinate refers to the score, and the abscissa refers to the number of days passed since the inoculation of a bacterium liquid. The black circle denotes the control group (vehicle), the white circle denotes AzaSite administered group, the black triangle denotes the 0.3% nanoized clarithromycin formulation administered group, the white triangle denotes the 1% nanoized clarithromycin formulation administered group, and the black square denotes the 1% clarithromycin bulk powder formulation administered group. The value refers to average values, and the error bar refers to the standard deviation.

FIG. 6 is a graph showing the results of drug efficacy test in accordance with evaluation criteria of Hatano et al. and Nakamura et al. The ordinate refers to the score, and the abscissa refers to the number of days passed since the inoculation of a bacterium liquid. The black circle denotes the control group (vehicle), the white circle denotes AzaSite administered group, the black triangle denotes the 0.3% nanoized clarithromycin formulation administered group, the white triangle denotes the 1% nanoized clarithromycin formulation administered group, and the black square denotes the 1% clarithromycin bulk powder formulation administered group. The value refers to average values, and the error bar refers to the standard deviation.

FIG. 7 is a graph showing the results of drug efficacy test in accordance with evaluation criteria of Draize et al. The ordinate refers to the score, and the abscissa refers to the number of days passed since the inoculation of a bacterium liquid. The black circle denotes the control group (vehicle), the white circle denotes AzaSite administered group, the black triangle denotes the 0.3% nanoized clarithromycin formulation administered group, the white triangle denotes the 1% nanoized clarithromycin formulation administered group, and the black square denotes the 1% clarithromycin bulk powder formulation administered group. The value refers to average values, and the error bar refers to the standard deviation.

DESCRIPTION OF EMBODIMENTS

1. Aqueous Suspension Formulation Comprising Fine Particles of a Macrolide Antibiotic The fine particle of a macrolide antibiotic can be produced by mixing a macrolide antibiotic, a physiologically acceptable salt and/or a physiologically acceptable saccharide, a physiologically acceptable polyol and/or water, and a dispersion stabilizer. The fine particle of a macrolide antibiotic of the present invention can be preferably produced by adding lecithin thereto during or after the pulverization step.

The polyol used for producing the fine particle of a macrolide antibiotic is not particularly limited as long as it is ingestible without causing any physiological problems. Preferably, the physiologically acceptable polyols are those which poorly solve salts, those with a high solubility to water, those with a low freezing point, and/or those with a high ignition point. For easy removal after pulverization, the physiologically acceptable polyol preferably has a high solubility to water.

The polyol includes, for example, glycerol, propylene glycol, polyethylene glycol, dipropylene glycol, and diethylene glycol, and preferably is propylene glycol or glycerol. The viscosity of polyol is preferably 1 to 100,000 (mPa·S), more preferably 5 to 10,000 (mPa·S), and further preferably 10 to 2,000 (mPa·S).

The amount of polyol used is preferably 0.2 to 50 parts by mass, more preferably 0.4 to 15 parts by mass, and further preferably 0.6 to 10 parts by mass, with respect to 1 part by mass of an organic compound to be pulverized. The kind of polyol used can be suitably determined according to the solubility of an organic compound to be pulverized. One kind of polyol may be used, or alternatively two or more kinds of polyol may be used in mixture.

The salt used for the production method of this embodiment is not particularly limited as long as it is ingestable without causing any physiological problems. The physiologically acceptable salts preferably have a poor solubility to polyols, a high solubility to water, and/or a low hygroscopicity, and a suitable hardness for fine pulverization of an organic compound. More preferably, the salt have two or more of these properties. The solubility degree of the salt to a polyol is preferably 10 (mass/vol) % or less. For easy removal of the salt after pulverization, the salt preferably has a high solubility to water.

Preferably, the salt include sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate, and dipotassium hydrogen phosphate. Preferably, the salt include sodium chloride, potassium chloride, magnesium sulfate, calcium sulfate, sodium citrate, sodium dihydrogen phosphate, potassium dihydrogen phosphate, disodium hydrogen phosphate, and dipotassium hydrogen phosphate, and more preferable salt is sodium chloride.

A particle diameter of a salt may be adjusted by pulverization, or the like, before mixing with a macrolide antibiotic. When adjusting the particle diameter of the salt in advance, the particle Dv may be, for example 5 to 300 µm, 10 to 200 µm, but preferably 0.01 to 300 µm, more preferably 0.1 to 100 µm, and further preferably 0.5 to 50 µm. The amount of the salt used is preferably 0 to 100 parts by mass, more preferably 0.2 to 50 parts by mass, and further preferably 0.5 to 30 parts by mass, with respect to 1 part by mass of an organic compound. One kind of salt may be used, or alternatively two or more kinds of salt may be used in mixture.

The fine particle of a macrolide antibiotic of the present invention is produced, for example, by carrying out the following steps in the order of "pulverizing step", "lecithin mixing step", "filtering and washing with water step", and "drying step". The "pulverizing step" and the "lecithin mixing step" may be integrated to be one step, wherein lecithin is added to the pulverized particles during pulverization of the particles. The suspension comprising the fine particles of a macrolide antibiotic can be preferably produced by adding a dispersant, if necessary, to the fine particles of a macrolide antibiotic obtained through any of the above steps, and by mixing the fine particles with water. For example, the suspension comprising the fine particles of a macrolide antibiotic can be produced by obtaining fine particles of a macrolide antibiotic through the steps of "pulverizing step" and "lecithin mixing step" without the steps of "filtering and washing with water step" and "drying step", adding a dispersant, if necessary, to the fine particles of a macrolide antibiotic, and mixing with water. The "pulverizing step", "lecithin mixing step", "filtering (separating) and washing with water step", and "drying step" are detailed in below.

(Pulverizing Step)

In the production method of the fine particles of a macrolide antibiotic, there is no particular limitation to a pulverizer used for wet pulverization of macrolide antibiotics as long as it can mechanically micronize macrolide antibiotics. The pulverizer can include commonly used pulverizers such as kneaders, two rolls, three rolls, fret mills, hoover mullers, disk blade kneader dispersers, and biaxial extruders.

The pulverization of a macrolide antibiotic can be preferably achieved by feeding an organic compound, a salt and a dispersion stabilizer into a pulverizer, and kneading them with gradually adding a polyol thereto. The viscosity at the time of kneading can be suitably determined depending on the kind of macrolide antibiotic to be pulverized, salt, and polyol. The temperature for pulverization can be suitably determined according to the macrolide antibiotic to be pulverized, the pulverizer, and the like. The temperature for pulverization is not particularly limited as long as it reduces the melting or decomposition of a macrolide antibiotic, and preferably −50 to 50° C., more preferably −20 to 30° C., and most preferably −10 to 25° C. The duration of pulverization can also be determined according to the macrolide antibiotic to be pulverized, the pulverizer, and the like. The duration of pulverization can be, for example, about 0.5 to 50 hours, is preferably 1 to 30 hours, more preferably 1.5 to 20 hours, and most preferably 2 to 10 hours.

The amount of the dispersion stabilizer used is preferably 0.002 to 10 parts by mass, more preferably 0.01 to 5 parts by mass, and further preferably 0.1 to 1 parts by mass, with respect to 1 part by mass of the macrolide antibiotic to be pulverized. The kind of the dispersion stabilizer used can be suitably determined according to the kind of organic compound to be pulverized. One kind of the dispersion stabilizer may be used, or alternatively two or more of different kind of stabilizer may be used in mixture.

(Lecithin Mixing Step)

Lecithin is mixed with the kneaded product during or after pulverization. The kneaded product does not necessary to contain a dispersion stabilizer. The lecithin mixing step can be carried out by adding lecithin in a pulverizer after or during pulverization, and continuing kneading in the same pulverizer. Alternatively, the lecithin mixing step can also be carried out with a different apparatus for mixing (a different mixer), by transferring the kneaded product after pulverization to the different mixer, adding lecithin thereto, and mixing the kneaded product with lecithin. The amount of lecithin used is preferably 0.01 to 10 parts by mass, more preferably 0.05 to 2 parts by mass, and further preferably 0.1 to 1.0 parts by mass, with respect to 1 part by mass of the macrolide antibiotic to be pulverized. Lecithin may be added singly, or alternatively added in the form of a mixture with a polyol. In the latter case, a mixing ratio (weight ratio) of a polyol to lecithin is 1 to 10 parts by mass, more preferably 1.5 to 5 parts by mass, and further preferably 2 to 4 parts by mass, with respect to 1 part by mass of lecithin.

(Filtering (Separating) and Washing with Water Step)

After mixing with lecithin, the salt and polyol are removed, if necessary, by filtration and washing with water. Specifically, the kneaded product after mixing with lecithin is added to a solvent, which is homogeneously mixed using a homogenizer or the like, followed by filtering and washing with water, whereby the salt and polyol can be removed. The solvent used for homogeneously mixing the kneaded product is not particularly limited, as long as the polyol and salt are easily dissolved, but the finely pulverized macrolide antibiotic is hardly dissolved, and it is a physiologically acceptable solvent. Water is preferable to be such a solvent, but other solvents may also be used. The solvent other than water include mixed solutions of water and an organic solvent such as acetic acid, methanol, or ethanol. The filtration method is not particularly limited and can be carried out by a well known method for filtering impurities contained in macrolide antibiotics. The filtration method include a filtration method under reduced pressure, a pressure filtration method, and a ultrafiltration membrane method. A centrifugal separation method can remove the salt and polyol as well as the filtration. Specifically, in the method of the centrifugal separation, the kneaded product after mixing lecithin is added to a solvent and homogeneously mixed using a homogenizer or the like, and subsequently the finely pulverized organic compound is precipitated using a centrifugal separator to remove the supernatant. The salt and polyol can be removed by repeating this procedure. The electrical conductivity of the supernatant can be measured to determine the timing to stop washing. More specifically, for example, when an electrical conductivity of the supernatant is 10 µS/cm, a sodium chloride concentration can be estimated to be about 5 ppm. The electrical conductivity at which washing is stopped may be determined according to the material properties.

The finely pulverized particles of a macrolide antibiotic usually have a high surface energy and thus easily aggregate. Thus, an additive for inhibiting a secondary aggregation may be added after removing the salt. The secondary aggregation inhibitor include alkyl sulfate, N-alkyloyl methyl taurine salts, ethanol, glycerol, propylene glycol, sodium citrate, purified soybean lecithin, phospholipids, D-sorbitol, lactose, xylitol, gum arabic, sucrose fatty acid ester, polyoxyethylene hydrogenated castor oil, polyoxyethylene fatty acid esters, polyethylene glycol, polyoxyethylene sorbitan fatty acid ester, alkyl benzene sulfonate, sulfosuccinate, polyoxyethylene polyoxypropylene glycol, polyvinylpyrrolidone (PVP), polyvinyl alcohol (PVA), hydroxypropyl cellulose (HPC), methyl cellulose (MC), hydroxyethyl cellulose (HEC), hydroxypropyl methyl cellulose (HPMC), carmellose sodium, carboxyvinyl polymer (CVP), N-acyl glutamate, acrylic acid copolymer, methacrylic acid copolymer, casein sodium, L-valine, L-leucine, L-isoleucine, benzalkonium chloride, and benzethonium chloride. Alkyl sulfate and N-alkyloyl methyl taurine salt are particularly preferable, and sodium dodecyl sulfate and sodium N-myristoyl methyl taurate are particularly preferable. One kind of a secondary aggregation inhibitor may be used, or alternatively two or more kind of secondary aggregation inhibitor may be used in mixture.

(Drying Step)

After removing the salt and polyol from the finely pulverized particles of macrolide antibiotic (in this specification, the term "removing" means not only a thorough removal but also a reduction to a certain extent), the solvent used for removing the salt, etc. can be removed from the finely pulverized particles of macrolide antibiotic by drying treatment, if necessary. The drying method is not particularly limited and can be a well known method for drying an organic compound. The drying method include a reduced pressure drying method, a freeze-drying method, a spray drying method, and a spray-freezing-drying method. The temperature, duration, and the like for drying are not particularly limited, but the temperature is preferably low for maintaining the chemical stability of a medicinal organic compound particle and preventing a secondary particle aggregation, and thus a preferable drying method is the reduced pressure drying method, the freeze-drying method, the spray drying method, and the spray-freezing-drying method.

(Suspension)

The fine particles of a macrolide antibiotic obtained after completing any of the steps "pulverizing step", "lecithin mixing step", "filtering and washing with water step", and "drying step" (e.g., the fine particles of a macrolide antibiotic obtained through the "pulverizing step" and "lecithin mixing step") can be mixed with a dispersant, if necessary, and mixed with water, and suspended by, if necessary, ultrasonic treatment.

The "average particle diameter" or "Dv" as referred herein means the arithmetic mean diameter in the particle diameter distribution measured by dynamic light scattering photon correlation spectroscopy. The 50% diameter (also referred to as median diameter, D50) refers to the particle diameter which divide the objective powders into two groups based on particle diameters so that the powders with larger diameter and the powders with smaller diameter have an equal amount. The "90% diameter" means the diameter of the particle at the 90% (D90) of total number of particles determined by counting the particles in ascending order from 0% (minimum) to 100% (maximum) of total number of particles using the particle diameter distribution measured by the above measurement method. The "10% diameter" means the diameter of the particle at the 10% (D10) of total number of particles determined by counting the particles in ascending order from 0% (minimum) to 100% (maximum) of the total number of particles using the particle diameter distribution measured by the above measurement method. Particularly when the aqueous suspension formulation described herein has viscosity, the average particle diameter (Dv) and the 90% diameter (D90) mean the average particle diameter (Dv) and the 90% diameter (D90) after the viscosity correction unless otherwise stated. The measurement method by dynamic light scattering photon correlation spectroscopy, the calculation method of particle diameter distribution, and the viscosity correction method are well known in the art.

2. Pharmaceutical Composition

The present invention relates to a pharmaceutical composition comprising the nanoparticles of a macrolide antibiotic. Preferably, the pharmaceutical composition of the present invention is a pharmaceutical composition for parenteral administration such as injections or formulations for topical application. The "topical formulation" as used herein means a formulation for the purpose of topical administration, or a formulation suitable for topical administration. The type of pharmaceutical composition used herein is not particularly limited and the dosage form include ocular topical formulation (e.g., eye drops), otic topical formulation (e.g., ear drops), nasal topical formulation (e.g., nose drops), suspensions, ointments, creams, gels, inhalers, and injections (e.g., injections for intravenous injection, injections for subcutaneous administration, injections for intramuscular injection, and intravenous drips). These formulations can be formulated by routine methods. The pharmaceutical composition of the present invention preferably contains a dispersion stabilizer. An injection is formulated by suspending the nanoparticles of a macrolide antibiotic of the present invention in water, or alternatively the nanoparticles may also be suspended, if necessary, in saline or a glucose solution. A dispersant, a buffer, or a preservative may further be added thereto. The pharmaceutical composition of the present invention can be formulated for parenteral administrations such as injections for intravenous administration, intramuscular administration, or subcutaneous administration, or such as intravenous drips, transdermal absorbers, transmucosal absorbers, eye drops, ear drops, nose drops, or inhalers.

The pharmaceutical composition of the present invention may contain a pharmacologically acceptable carrier (a pharmaceutical additive). The kind of pharmaceutical additives used for producing the pharmaceutical composition, the proportion of the pharmaceutical additives with respect to the effective ingredient, or the method for producing the pharmaceutical composition may be suitably selected by the person skilled in the art depending on the form of composition. The pharmaceutical additives used may be inorganic or organic substances, or solid or liquid substances, and commonly added in the proportion from 1 wt % to 90 wt % with respect to a weight of the effective ingredient. Specific examples of such a substance include lactose, glucose, mannitol, dextrin, cyclodextrin, starch, sucrose, magnesium aluminometasilicate, synthetic aluminum silicate, sodium carboxymethyl cellulose, hydroxypropyl starch, carboxymethyl cellulose calcium, ion exchange resin, methyl cellulose (MC), gelatin, gum arabic, hydroxypropyl cellulose (HPC), hydroxypropyl methyl cellulose (HPMC), polyvinylpyrrolidone (PVP), polyvinyl alcohol (PVA), light anhydrous silicic acid, magnesium stearate, talc, tragacanth, bentonite, veegum, titanium oxide, sorbitan fatty acid ester, sodium lauryl sulfate, glycerol, glycerol fatty acid ester, purified lanolin, glycerogelatin, polysorbate, Macrogol, vegetable oils, waxes, liquid paraffin, white vaseline, fluorocarbon, nonionic surfactants, propylene glycol, water, benzalkonium chloride, hydrochloric acid, sodium chloride, sodium hydroxide, lactic acid, sodium, sodium monohydrogen phosphate, sodium dihydrogen phosphate, citric acid, sodium citrate, disodium edetate, poloxamer 407, and polycarbophil.

The aqueous suspension formulation or pharmaceutical composition of the present invention can be enclosed, in the form of a kit, with an outer package, a container, a diluent, a suspension agent, and/or an instructions insert on the formulation method and administration method. When the aqueous suspension formulation or pharmaceutical composition of the present invention is supplied in the form of a kit, different components of the aqueous suspension formulation or pharmaceutical composition may be packed in separate containers and enclosed in a single kit. Alternatively, at least one of a part of the components of the aqueous suspension formulation or pharmaceutical composition (at least including the nanoparticles of a macrolide antibiotic) may only be included in a kit and other components may be provided separately from the kit. When the aqueous suspension formulation or pharmaceutical composition of the present invention is supplied as the kit, the necessary components can be preferably mixed immediately before use to obtain the aqueous suspension formulation or pharmaceutical composition of the present invention.

For example, the kit of the present invention can be kits as follows:

(a) a kit comprising nanoparticles of a macrolide antibiotic for preparing a pharmaceutical composition comprising the nanoparticles of the macrolide antibiotic; or a kit comprising an aqueous suspension formulation comprising nanoparticles of a macrolide antibiotic for preparing a pharmaceutical composition comprising the nanoparticles of the macrolide antibiotic, (b) the kit of (a), wherein the average particle diameter of the nanoparticles is 500 nm or less and the D90 particle diameter is 1500 nm or less;

(c) the kit of (a) or (b), wherein the nanoparticles are produced by mixing a macrolide antibiotic, a physiologically acceptable salt and/or a physiologically acceptable saccharide, a physiologically acceptable polyol and/or water, and a dispersion stabilizer;

(d) the kit of any one of (a) to (c), wherein the macrolide antibiotic is erythromycin, clarithromycin, roxithromycin, azithromycin, josamycin, rokitamycin, or kitasamycin;

(e) the kit of any one of (a) to (d), comprising a dispersion stabilizer;

(f) the kit of (e), wherein the dispersion stabilizer is a surfactant, an aggregation inhibitor, and/or a viscosity modifier;

(g) the kit of (f), wherein the surfactant is polyoxyethylene hydrogenated castor oil 60, polysorbate 80, polyethylene glycol monostearate, and/or polyoxyethylene polyoxypropylene glycol;

(h) the kit of (f), wherein the aggregation inhibitor is polyvinyl alcohol, polyethylene glycol, and/or polyvinylpyrrolidone;

(i) the kit of (f), wherein the viscosity modifier is methyl cellulose, hydroxypropyl methyl cellulose, and/or hydroxyethyl cellulose;

(j) the kit of any one of (a) to (i), wherein the pharmaceutical composition comprising the nanoparticles of a macrolide antibiotic has low irritability;

(k) the kit of any one of (a) to (j), comprising the nanoparticles of a macrolide antibiotic in the form of the aqueous suspension formulation;

(l) the kit of any one of (a) to (k) for preparing a pharmaceutical composition for a parenteral administration;

(m) the kit of (l) for preparing an injection or a formulation for topical application;

(n) the kit of (m) for preparing an ocular topical formulation, an otic topical formulation, a nasal topical formulation, or a pulmonary topical formulation;

(o) the kit of (n) for preparing an eye drop, an ear drop, a nose drop, or an inhaler;

(p) the kit of any one of (a) to (o) for preparing a therapeutic drug or a preventive drug for inflammatory diseases or infectious diseases of the eye, ear, nose or lung.

Accordingly, in an embodiment, the present invention may be a method for preparing an aqueous pharmaceutical composition comprising nanoparticles of a macrolide antibiotic, comprising mixing a diluent and the aqueous suspension formulation comprising the nanoparticles of the macrolide antibiotic. Alternatively, the present invention may also be a method for preparing an aqueous suspension formulation or an aqueous pharmaceutical composition which comprises the nanoparticles of a macrolide antibiotic, comprising mixing a suspension agent and the nanoparticles of a macrolide antibiotic.

In preparing the pharmaceutical composition (e.g., injections, ocular topical formulation (preferably eye drops), otic topical formulation (preferably ear drops), nasal topical formulation (preferably nose drops), or pulmonary topical formulation (preferably inhalers)) of the present invention, the pH and osmotic pressure thereof are not particularly limited as long as they are within the extent acceptable for the topical formulations, and preferably pH 5 to 9.5, more preferably pH 6 to 9, further preferably pH 7 to 9. The ratio of osmotic pressure of the formulation (ointments are excluded) to saline is, for example, about 0.3 to 4.3, preferably about 0.3 to 2.2, particularly preferably about 0.5 to 1.5. The pH and osmotic pressure may be regulated using a pH controller, a tonicity agent, a salt, or the like by using a method well known in the art.

Herein, the suspension agent and/or diluent can contain water as the main ingredient. Also, the pharmaceutical composition, suspension agent and/or the diluent may contain various additives, if necessary, such as a thickener, a surfactant, a preservative, a disinfectant or antibacterial agent, a pH controller, a tonicity agent, and a buffer.

The preservative and disinfectant or antibacterial agent include such as sorbic acid or salts thereof (sorbic acid, potassium sorbate, sodium sorbate, triclocarban sorbate, and the like), paraoxybenzoates (methyl parahydroxybenzoate, ethyl parahydroxybenzoate, propyl parahydroxybenzoate, butyl parahydroxybenzoate, and the like), acrinol, methylrosanilinium chloride, benzalkonium chloride, benzethonium chloride, cetylpyridinium chloride, cetylpyridinium bromide, chlorhexidine or salts thereof, polyhexamethylene biguanide, alkylpolyaminoethylglycine, benzyl alcohol, phenethyl alcohol, chlorobutanol, isopropanol, ethanol, phenoxyethanol, silver supported on zirconium phosphate, mercurochrome, povidone iodine, thimerosal, dehydroacetic acid, chloroxylenol, chlorophen, resorcinol, orthophenylphenol, isopropylmethylphenol, thymol, hinokitiol, sulfamine, lysozyme, lactoferrin, triclosan, 8-hydroxyquinoline, undecylenic acid, caprylic acid, propionic acid, benzoic acid, halocarban, thiabendazole, polymyxin B, 5-chloro-2-methyl-4-isothiazolin-3-one, 2-methyl-4-isothiazolin-3-one, polylysine, hydrogen peroxide, polydronium chloride, Glokill (tradename: e.g., Glokill PQ, produced by Rhodia), polydiaryl dimethyl ammonium chloride, poly[oxyethylene (dimethyliminio)ethylene-(dimethyliminio)ethylene dichloride], polyethylene polyamine-dimethylamine epichlorohydrin polycondensates (tradename: e.g., Busan 1157, produced by Buckman Laboratories International, Inc.), biguanide compounds (Cosmosil CQ (tradename, about 20 wt % content of polyhexamethylenebiguanide hydrochloride, produced by Arch Personal Care Products L.P.), and the like, and pharmacologically acceptable salts thereof.

The pH controller include inorganic acids (hydrochloric acid, sulfuric acid, phosphoric acid, polyphosphoric acid, boric acid, and the like), organic acids (lactic acid, acetic acid, citric acid, tartaric acid, malic acid, succinic acid, oxalic acid, gluconic acid, fumaric acid, propionic acid, acetic acid, aspartic acid, epsilon-aminocaproic acid, glutamic acid, and aminoethylsulfonic acid, and the like), gluconolactone, ammonium acetate, inorganic bases (sodium hydrogencarbonate, sodium carbonate, potassium hydroxide, sodium hydroxide, calcium hydroxide, and magnesium hydroxide, and the like), organic bases (monoethanolamine, triethanolamine, diisopropanolamine, triisopropanolamine, and lysine, and the like), borax, and pharmacologically acceptable salts thereof.

The tonicity agent include inorganic salts (e.g., sodium chloride, potassium chloride, sodium carbonate, sodium hydrogencarbonate, calcium chloride, magnesium sulfate, sodium hydrogen phosphate, disodium hydrogen phosphate, dipotassium hydrogen phosphate, sodium thiosulfate, and sodium acetate), polyhydric alcohols (e.g., glycerol, propylene glycol, ethylene glycol, and 1,3-butylene glycol), saccharides (e.g., glucose, mannitol, and sorbitol).

The buffer include tris buffer, borate buffer, phosphate buffer, carbonate buffer, citrate buffer, acetate buffer, epsilon-aminocaproic acid, and aspartate. Specifically the buffer may be boric acid or salts thereof (odium borate, potassium tetraborate, potassium metaborate, and the like), phosphoric acid or salts thereof (sodium hydrogen phosphate, sodium dihydrogen phosphate, potassium dihydrogen phosphate, and the like), carbonic acid or salts thereof (sodium hydrogencarbonate, sodium carbonate, and the like), citric acid or salts thereof (sodium citrate, potassium citrate, and the like).

The pharmaceutical composition of the present invention can be prepared by a well known method. For example, an aqueous suspension formulation comprising nanoparticles of a macrolide antibacterial agent is mixed with any other components in a suitable diluent such as distilled water or purified water, and then the osmotic pressure and pH are controlled as described above, which is subsequently sterilized by high pressure steam or filtration under sterile environment, followed by filling aseptically into a washed and sterilized container.

The pharmaceutical composition of the present invention can be a therapeutic drug or a preventive drug for inflammatory diseases or infectious diseases. For example, the pharmaceutical composition of the present invention can be a therapeutic or preventive drug for inflammatory diseases or infectious diseases caused by infections. Thus, the present invention encompasses an aqueous suspension formulation for use as a medicament (a therapeutic drug or a preventive drug for inflammatory diseases or infectious diseases), comprising nanoparticles of a macrolide antibiotic and a dispersion stabilizer.

The inflammatory diseases or infectious diseases herein encompass systemic inflammatory diseases and infectious diseases as well as the topical inflammatory diseases and infectious diseases. The inflammatory diseases include, in addition to the inflammatory diseases caused by infections, allergic inflammatory diseases (e.g., allergic rhinitis, allergic conjunctivitis, allergic dermatitis, allergic eczema, allergic asthma, and allergic pneumonia). The systemic inflammatory disease includes systemic inflammatory diseases and infectious diseases such as superficial/deep skin infections, lymphangitis/lymphadenitis, mastitis, steomyelitis, tonsillitis, pneumonia, pyelonephritis, urethritis, gonococal infection, syphilis, intrauterine infection, scarlet fever, diphtheria, whooping cough, secondary infections from external wound, skin burn, surgeries, and the like, pharyngitis/laryngitis, bronchitis, secondary infections from chronic respiratory diseases, pericoronitis, periodontal inflammation, tetanus, cystitis, prostatitis, infectious enteritis, jaw inflammation, infectious arthritis, and gastritis.

Specifically, the pharmaceutical composition of the present invention can be used for treating or preventing inflammatory diseases and infectious diseases of the eye and various conditions associated therewith. The inflammatory diseases and infectious diseases of the eye can include eyelid symptoms including blepharitis, blepharoconjunctivitis, meibomitis, acute or chronic stye, chalazion, dacryocystitis, dacryoadenitis, and acne rosacea; conjunctiva symptoms including conjunctivitis, nophthalmia neonatorum, and trachoma; cornea symptoms including corneal ulcer, superficial keratitis and keratitis parenchymatosa, keratoconjunctivitis, foreign objects, and post-operative infections; and anterior chamber and uvea symptoms including endophthalmitis, infectious uveitis, and post-operative infections. The preventions of infections include the administration of the pharmaceutical composition before surgical treatment such as an operation or before contacting a person presenting infectious symptoms. For the preventive use, the pharmaceutical composition can be administered before surgical treatment such as blepharoplasty, chalazion removal, blepharorrhaphy, surgeries for canaliculi and lacrimal drainage system, and other surgical treatment relating to eyelids and lacrimal apparatus; conjunctival surgeries including removal of pterygium, pinguecula, and tumors, traumatic wounds such as conjunctival transplant, cuts, burns, and scratches, and conjunctival flap surgery; corneal surgeries including removal of foreign objects, keratotomy, and corneal transplant; refractive surgeries including photorefractive procedure; glaucoma surgeries including bleb filtration; paracentesis of anterior chamber; iridotomy; cataract surgery; retinal surgery; and extraocular muscle relating surgeries. The prevention of nophthalmia neonatorum is also included in the prevention of this specification.

For example, the pharmaceutical composition of the present invention can be used for treating or preventing various conditions associated with inflammatory diseases or infectious diseases of the ear. The inflammatory disease or infectious disease of the ear include otitis media and otitis externa. The prevention of infection include a presurgical treatment given before a surgery, and a treatment before other infection causable conditions or contacting a person with infectious disease. The preventive situation includes a treatment before surgery involving an external wound or injury of the ear, and a treatment before other surgeries or operations.

The pharmaceutical composition of the present invention can be used for treatment or prevention of various conditions associated with inflammatory diseases or infectious diseases of a nose. In the entire description, the term "nose" as used for the "inflammatory disease or infectious disease of a nose" and the "nasal topical formulation" includes an entire upper respiratory tract such as a nasal cavity, nasopharynx, pharynx, and larynx. The inflammatory disease or infectious disease of a nose includes sinusitis, allergic rhinitis, and rhinitis.

The pharmaceutical composition of the present invention can be used for treatment or prevention of various conditions associated with inflammatory diseases or infectious diseases of the lung. In the entire description, the term "lung" as used for the "inflammatory disease or infectious disease of the lung" and the "pulmonary topical formulation" includes an entire lower respiratory tract such as a trachea, brunchus, bronchiole, and lung. The inflammatory disease or infectious disease of the lung includes pneumonia, bronchitis, allergic pneumonia, and asthma.

More preferably, the pharmaceutical composition of the present invention can be used for treatment or prevention of infectious diseases (e.g., infectious diseases of the eye, ear, nose or lung) caused by a wide variety of bacteria or parasite. Such microorganism includes the *Staphylococcus* genus including *Staphylococcus aureus* and *Staphylococcus epidermidis*; the *Streptococcus* genus including *Streptococcus pneumoniae* and *Streptococcus pyogenes*, Groups C, F, and G Streptococci, and Group viridans *Streptococcus; Haemophilus influenzae* including biotype III; *Haemophilus ducreyi; Moraxella catarrhalis*; the *Neisseria* genus including *Neisseria gonorrhoeae* and *Neisseria meningitidis*; the *Chlamydia* genus including *Chlamydia trachomatis, Chlamydia psittaci*, and *Chlamydia pneumoniae*; the *Mycobacterium* genus including atypical Mycobacteria including *Mycobacterium tuberculosis* and *Mycobacterium tubercule bacillus* intracellular complex, and *Mycobacterium marinum, Mycobacterium fortuitum*, and *Mycobacterium chelonae; Bordetella pertussis; Campylobacter jejuni; Legionella pneumophila; Bacteroides bivius; Welch bacillus; Peptostreptococcus* species; *Borrelia burgdorferi; Myco-* plasma pneumonia; *Treponema pallidum*; *Ureaplasma urealyticum*; *toxoplasma*; *malaria*; and *nosema*.

3. Treatment/Preventive Method

The pharmaceutical composition of the present invention can be used for treatment or prevention of an inflammatory disease or an infectious disease by administering in an effective dose to a subject in need thereof. The present invention relates to a method of treatment or prevention of an inflammatory disease or an infectious disease, comprising administering an effective dose of the pharmaceutical composition comprising an aqueous suspension formulation including nanoparticles of a macrolide antibiotic (and a dispersion stabilizer) to a subject in need thereof. A subject can be any animals classified in the mammals such as human; companion animals such as dog, cat, and rabbit; domestic animals such as cow, pig, sheep, and horse, and preferably is human.

An dosage amount and number of dose of administration of the pharmaceutical composition of the present invention are not particularly limited and can suitably be selected by a physician's discretion depending on the purpose of prevention and/or treatment of deterioration/progress of the disease to be treated, the type of disease, a patient's conditions such as the body weight and age. The dosage amount is generally about 0.01 to 1000 mg (as an effective ingredient weight) per day for an adult, and number of dose can be once or several times per day. The administration route is an injection or topical administration, including intravenous injections, intramuscular injections, or subcutaneous injections, intravenous drips, eye drops, ear drops, nose drops, transdermal administration, transmucosal administration, or inhalers.

When the pharmaceutical composition of the present invention is an injection, it can be administered continuously or intermittently at a dose of 0.001 to 100 mg (as an effective ingredient weigh) per day for an adult.

When the aqueous pharmaceutical composition of the present invention is for topical administration, it is directly administered locally to an affected area, an area around an affected area, an organ with an affected area, or the like. For example, the pharmaceutical composition of the present invention can be formulated into an ocular topical formulation, an otic topical formulation, a nasal topical formulation, or a pulmonary topical formulation. The pharmaceutical composition of the present invention in topical formulation can be applied everyday, or in any number of dose after development of a local inflammatory disease or infectious disease. The dosage amount can be suitably adjusted depending on conditions, etc. Usually, it is administered to an eye once to 6 times per day with about 1 to 3 drops per one time.

Hereinafter, the present invention is described in more detail with reference to examples, but these Examples do not intend to limit the scope of the present invention. All of the documents referred to herein are incorporated in their entirety by reference.

Example 1

Production of Pulverized Clarithromycin Dough

To a 0.5 L TRI-MIX (INOUE MFG., INC.), 10 g of clarithromycin having an average particle diameter of 10,370 nm (melting point: 217 to 220° C.; Assia Chemical Industries Ltd.), 10 g of pulverized sodium chloride (average particle diameter: 5 μm), 60 g of mannitol (Wako Pure Chemical Industries, Ltd.), 3 g of polyvinylpyrrolidone K25 (Wako Pure Chemical Industries, Ltd.), and 5 g of hydrogenated soybean lecithin PHOSPHOLIPON 90H (H. Holstein Co., Ltd.) were fed and homogeneously mixed, and then 20 g of glycerol was added thereto, which was pulverized at 5° C. for 5 hours with maintaining the content in the dough state. The obtained kneaded dough had a recovered amount of 93 g (yield 86%).

To 100 mg of the obtained kneaded dough, 3 g of 0.1% HCO-60 (Nihon Surfactant Kogyo K.K.) was added and dispersed for several minutes using a bathtub type ultrasonic disperser (VS-100III, AS ONE Corporation). As a result of measuring the particle diameter distributions of clarithromycin by using a particle diameter distribution counter (DelsaNano, Beckman Coulter, Inc.), the average particle diameter (Dv) was 144.7 nm, the 10% diameter (D10) was 81.4 nm, the 50% diameter (D50) was 124.6 nm, and the 90% diameter (D90) was 197.0 nm.

Example 2

Effect of Dispersant (Surfactant)

(1) Production of a Clarithromycin 0.1% Formulation (HCO-60)

After pulverization by the TRI-MIX as described in Example 1, 0.5 g of the clarithromycin kneaded product (kneaded dough) was weighed in a 50 mL-glass vial, to which 44 g of an aqueous 0.1% HCO-60 (Nihon Surfactant Kogyo K.K.) solution was added, and then dispersed for 1 to 2 minutes using a bathtub type ultrasonic disperser (VS-100M, AS ONE Corporation), followed by further dispersion for 1 minute using a probe-type ultrasonic disperser (S-4000, MISONIX). As a result of measuring the particle diameter distributions of clarithromycin in the aqueous dispersion by using a particle diameter distribution counter (DelsaNano, Beckman Coulter, Inc., the same applies to hereinbelow), the average particle diameter (Dv) was 146.0 nm, the 10% diameter (D10) was 72.5 nm, the 50% diameter (D50) was 119.2 nm, and the 90% diameter (D90) was 220.3 nm.

(2) Production of a Clarithromycin 0.1% Formulation (Tween 80)

The same procedure was carried out as in the Example 2 (1), except that the "0.1% HCO-60 (Nihon Surfactant Kogyo K.K.)" used in the above Example 2 (1) was replaced with "0.1% Tween 80 (Kanto Chemical Co., Inc.)". The particle diameter distributions of clarithromycin were the average particle diameter (Dv) of 198.5 nm, the 10% diameter (D10) of 84.3 nm, the 50% diameter (D50) of 154.9 nm, and the 90% diameter (D90) of 291.3 nm.

(3) Production of a Clarithromycin 0.1% Formulation (MYS-40)

The same procedure was carried out as in Example 2 (1), except that the "0.1% HCO-60 (Nihon Surfactant Kogyo K.K.)" used in the above Example 2 (1) was replaced with "0.1% MYS-40 (Nihon Surfactant Kogyo K.K.)". The particle diameter distributions of clarithromycin were the average particle diameter (Dv) of 142.2 nm, the 10% diameter (D10) of 72.4 nm, the 50% diameter (D50) of 118.8 nm, and the 90% diameter (D90) of 208.1 nm.

Example 3

Stability Test of Nanoized Clarithromycin Aqueous Dispersion

About 4 mL each of the aqueous dispersions of the nanoized clarithromycin produced in Example 2 was poured into a 9 mL-screw vial, and after firmly closing the cap, the vials were stored at room temperature for one day, which were evaluated for the stability by visual observation, etc. The results are shown in Table 1. The obtained results suggest that HCO-60 excels as a dispersant.

TABLE 1

| | Example 2 | | |
|---|---|---|---|
| | (1) | (2) Dispersant | (3) |
| | HCO-60 | Tween80 | MYS-40 |
| Amount of deposits | Little | Much | Much |
| Clarity | High | Turbid | Turbid |
| Microscopic observation | No aggregates or crystal | Aggregates observed | Crystals observed |
| Overall evaluation | o | x | x |

Example 4

Effect of Thickeners (1) Production of a Clarithromycin 0.1% Formulation (HPMC 60SH-50)

After pulverization by the TRI-MIX in Example 1, 1 g of the clarithromycin kneaded product (kneaded dough) was weighed in a 50 mL-glass vial, to which 44 g of an aqueous 0.1% HCO-60 solution was added, and then dispersed for 1 to 2 minutes using a bathtub type ultrasonic disperser (VS-100III, AS ONE Corporation), followed by further dispersion under applied pressure (90 MPa) using a high-pressure homogenizer (L01, Sanwa Engineering Co, Ltd.). As a result of measuring the particle diameter distributions of clarithromycin in the aqueous dispersion using a particle diameter distribution counter, the average particle diameter (Dv) was 154.9 nm, the 10% diameter (D10) was 77.1 nm, the 50% diameter (D50) was 113.2 nm, and the 90% diameter (D90) was 224.9 nm.

To the obtained aqueous dispersion, 22 g of an aqueous 0.9% HPMC 60SH-50 solution was added, which was stirred using a magnetic stirrer, and then adjusted to be 89 g with purified water and mixed by stirring to produce the final formulation. As a result of measuring the particle diameter distributions of clarithromycin in the formulation using a particle diameter distribution counter, the average particle diameter (Dv) was 327.8 nm, the 10% diameter (D10) was 189.5 nm, the 50% diameter (D50) was 284.4 nm, and the 90% diameter (D90) was 423.0 nm. Further, as the result of recalculating the particle diameter distributions by the viscosity correction, the average particle diameter (Dv) was 170.1 nm, the 10% diameter (D10) was 98.6 nm, the 50% diameter (D50) was 148.6 nm, and the 90% diameter (D90) was 223.3 nm.

(2) Production of a Clarithromycin 0.1% Formulation (HPMC 60SH-4000)

The same procedure was carried out as in the Example 4 (1), except that the "22 g of an aqueous 0.9% HPMC 60SH-50 solution was added, which was stirred using a magnetic stirrer" as in the Example 4 (1) was replaced with "22 g of an aqueous 0.9% HPMC 60SH-4000 (Shin-Etsu Chemical Co., Ltd.) solution was added, which was dispersed for 1 minute using a probe-type ultrasonic disperser (S-4000, MISONIX)" to produce the final formulation. The particle diameter distributions before the viscosity correction were the average particle diameter (Dv) of 1017.7 nm, the 10% diameter (D10) of 441.8 nm, the 50% diameter (D50) of 818.3 nm, and the 90% diameter (D90) of 1629.6 nm. The particle diameter distributions after the viscosity correction were the average particle diameter (Dv) of 219.4 nm, the 10% diameter (D10) of 98.5 nm, the 50% diameter (D50) of 183.6 nm, and the 90% diameter (D90) of 370.2 nm.

(3) Production of a Clarithromycin 0.1% Formulation (HPMC 65SH-4000)

The same procedure was carried out as in the Example 4 (2), except that the "22 g of an aqueous 0.9% HPMC 60SH-4000 solution was added" as in the Example 4 (2) was replaced with "23 g of an aqueous 1% HPMC 65SH-4000 (Shin-Etsu Chemical Co., Ltd.) solution was added" to produce the final formulation. The particle diameter distributions before the viscosity correction were the average particle diameter (Dv) of 990.1 nm, the 10% diameter (D10) of 424.8 nm, the 50% diameter (D50) of 840.2 nm, and the 90% diameter (D90) of 1565.5 nm. The particle diameter distributions after the viscosity correction were the average particle diameter (Dv) of 219.4 nm, the 10% diameter (D10) of 93.5 nm, the 50% diameter (D50) of 183.4 nm, and the 90% diameter (D90) of 342.0 nm.

(4) Production of a Clarithromycin 0.1% Formulation (HPMC 90SH-4000SR)

The same procedure was carried out as in the Example 4 (2), except that the "22 g of an aqueous 0.9% HPMC 60SH-4000 solution was added" as in the Example 4 (2) was replaced with "8 g of an aqueous 1% HPMC 90SH-4000SR (Shin-Etsu Chemical Co., Ltd.) solution was added" to produce the final formulation. The particle diameter distributions before the viscosity correction were the average particle diameter (Dv) of 425.0 nm, the 10% diameter (D10) of 146.9 nm, the 50% diameter (D50) of 332.6 nm, and the 90% diameter (D90) of 715.6 nm. The particle diameter distributions after the viscosity correction were the average particle diameter (Dv) of 219.4 nm, the 10% diameter (D10) of 71.1 nm, the 50% diameter (D50) of 157.7 nm, and the 90% diameter (D90) of 334.4 nm.

(5) Production of a Clarithromycin 0.1% Formulation (MC SM-15)

The same procedure was carried out as in the Example 4 (1), except that the "22 g of an aqueous 0.9% HPMC 60SH-50 solution was added" as in the Example 4 (1) was replaced with "33 g of an aqueous 1% MC SM-15 (Shin-Etsu Chemical Co., Ltd.) solution was added" to produce the final formulation. The particle diameter distributions before the viscosity correction were the average particle diameter (Dv) of 325.5 nm, the 10% diameter (D10) of 158.1 nm, the 50% diameter (D50) of 271.3 nm, and the 90% diameter (D90) of 474.8 nm. The particle diameter distributions after the viscosity correction were the average particle diameter (Dv) of 167.8 nm, the 10% diameter (D10) of 81.4 nm, the 50% diameter (D50) of 141.1 nm, and the 90% diameter (D90) of 246.9 nm.

(6) Production of a Clarithromycin 0.1% Formulation (MC SM-100)

The same procedure was carried out as in the Example 4 (1), except that the "22 g of an aqueous 0.9% HPMC 60SH-50 solution was added" as in the Example 4 (1) was replaced with "33 g of an aqueous 1% MC SM-100 (Shin-Etsu Chemical Co., Ltd.) solution was added" to produce the final formulation. The particle diameter distributions before the viscosity correction were the average particle diameter (Dv) of 608.4 nm, the 10% diameter (D10) of 258.8 nm, the 50% diameter (D50) of 499.1 nm, and the 90% diameter (D90) of 979.6 nm. The particle diameter distributions after the viscosity correction were the average particle diameter (Dv) of 199.8 nm, the 10% diameter (D10) of 81.6 nm, the 50% diameter (D50) of 160.5 nm, and the 90% diameter (D90) of 321.3 nm.

(7) Production of a Clarithromycin 0.1% Formulation (PVA-204C)

The same procedure was carried out as in the Example 4 (1), except that the "22 g of an aqueous 0.9% HPMC 60SH-50 solution was added" as in the Example 4 (1) was replaced with "33 g of an aqueous 2% PVA-204C (Kuraray Co., Ltd.) solution was added" to produce the final formulation. The particle diameter distributions before the viscosity correction were the average particle diameter (Dv) of 197.1 nm, the 10% diameter (D10) of 109.3 nm, the 50% diameter (D50) of 169.1 nm, and the 90% diameter (D90) of 268.6 nm. The particle diameter distributions after the viscosity correction were the average particle diameter (Dv) of 142.4 nm, the 10% diameter (D10) of 80.1 nm, the 50% diameter (D50) of 123.3 nm, and the 90% diameter (D90) of 196.1 nm.

(8) Production of a Clarithromycin 0.1% Formulation (PEG-4000)

The same procedure was carried out as in the Example 4 (1), except that the "22 g of an aqueous 0.9% HPMC 60SH-50 solution was added" as in the Example 4 (1) was replaced with "33 g of an aqueous 2% PEG-4000 (Kanto Chemical Co., Inc.) solution was added" to produce the final formulation. The particle diameter distributions before the viscosity correction were the average particle diameter (Dv) of 160.6 nm, the 10% diameter (D10) of 82.1 nm, the 50% diameter (D50) of 133.1 nm, and the 90% diameter (D90) of 235.6 nm. The particle diameter distributions after the viscosity correction were the average particle diameter (Dv) of 149.4 nm, the 10% diameter (D10) of 68.0 nm, the 50% diameter (D50) of 110.3 nm, and the 90% diameter (D90) of 201.1 nm.

(9) Production of a Clarithromycin 0.1% Formulation (PVP K30)

The same procedure was carried out as in the Example 4 (1), except that the "22 g of an aqueous 0.9% HPMC 60SH-50 solution was added" as in the above Example 4 (1) was replaced with "33 g of an aqueous 4% PVP K30 (Wako Pure Chemical Industries, Ltd.) solution was added" to produce the final formulation. The particle diameter distributions before the viscosity correction were the average particle diameter (Dv) of 212.7 nm, the 10% diameter (D10) of 108.2 nm, the 50% diameter (D50) of 176.4 nm, and the 90% diameter (D90) of 309.4 nm. The particle diameter distributions after the viscosity correction were the average particle diameter (Dv) of 157.0 nm, the 10% diameter (D10) of 78.9 nm, the 50% diameter (D50) of 130.4 nm, and the 90% diameter (D90) of 231.4 nm.

Example 5

Stability Test of Formulations (1) Influence by Thickeners to the Stability 1

About 4 mL each of the aqueous dispersions of the nanoized clarithromycin produced in Example 4 was poured into a 9 mL-screw vial, and after firmly closing the cap, the vials were stored at 40° C. for 7 days, which were evaluated for the stability by visual observation, etc. The results are shown in Table 2. The obtained results suggest that HPMC (60SH-50) and MC (SM15) excel as a thickener.

TABLE 2

| | Example 4 | | | | |
|---|---|---|---|---|---|
| | (1) | (5) | (7) | (8) | (9) |
| | | | Thickener | | |
| | HPMC (60SH-50) | MC (SM-15) | PVA | PEG-4000 | PVP-K30 |
| Amount of deposits | None | None | Much | Much | Much |
| Clarity | High | High | Turbid | Turbid | Low |
| Microscopic observation | No aggregates or crystal | No aggregates or crystal | Capillary crystal observed | Capillary crystal observed | Capillary crystal observed |
| Overall evaluation | ○ | ○ | x | x | x |

(2) Influence by Thickeners to the Stability 2

Example 5 (1) revealed the excellence of HPMC and MC as thickeners. A further test was conducted to examine the influence to the stability by the type of HPMC and MC. About 4 mL each of the dispersions of the nanoized clarithromycin produced in Example 4 was poured into a 9 mL-screw vial, and after firmly closing the cap, the vials were stored at 25° C. for 14 days, which were evaluated for the stability by visual observation, etc. The results are shown in Table 3. The results suggest that all of the HPMC series and MC series used in Example 4 (2), (3), (4), and (6) are suitable as a thickener.

TABLE 3

| | Example 4 | | | |
|---|---|---|---|---|
| | (2) | (3) | (4) | (6) |
| | | | Thickener | |
| | HPMC (60SH-4000) | HPMC (65SH-4000) | HPMC (90SH-4000SR) | MC (SM-100) |
| Amount of deposits | None | None | None | None |
| Clarity | High | High | High | High |
| Microscopic observation | No aggregates or crystal | No aggregates or crystal | No aggregates or crystal | No aggregates or crystal |
| Overall evaluation | ○ | ○ | ○ | ○ |

Example 6

In Vitro Antibacterial Test (Minimum Inhibitory Concentration Test)

(1) Formulation Production: Production of a Clarithromycin 0.3% Formulation

After pulverization by the TRI-MIX in Example 1, 3 g of the clarithromycin kneaded product (kneaded dough) was weighed in a 50 mL-glass vial, to which 10 g of an aqueous 1% HCO-60 solution was added, and then dispersed for 1 to 2 minutes using a bathtub type ultrasonic disperser (VS-100III, AS ONE Corporation), followed by further dispersion for 1 minute using a probe-type ultrasonic disperser (S-4000, MISONIX). As a result of measuring the particle diameter distributions of clarithromycin in the dispersion using a particle diameter distribution counter, the average particle diameter (Dv) was 246.0 nm, the 10% diameter (D10) was 103.7 nm, the 50% diameter (D50) was 196.4 nm, and the 90% diameter (D90) was 393.8 nm.

To the obtained aqueous dispersion, 22 g of an aqueous 0.9% HPMC 60SH-50 solution was added, which was stirred using a magnetic stirrer, and then adjusted to be 89 g with purified water and mixed by stirring to produce the final formulation. As a result of measuring the particle diameter distributions of clarithromycin in the formulation using a particle diameter distribution counter, the average particle diameter (Dv) was 328.9 nm, the 10% diameter (D10) was 167.3 nm, the 50% diameter (D50) was 270.4 nm, and the 90% diameter (D90) was 481.2 nm. Further, as the result of recalculating the particle diameter distributions by the viscosity correction, the average particle diameter (Dv) was 162.4 nm, the 10% diameter (D10) was 82.0 nm, the 50% diameter (D50) was 133.6 nm, and the 90% diameter (D90) was 239.9 nm.

(2) Minimum Inhibitory Concentration (MIC) Test

An MIC test was conducted by applying the minimum inhibitory concentration (MIC) measurement method by the broth microdilution method (the standard method of Japanese Society of Chemotherapy). The clarithromycin suspension prepared in Example 6 (1) (test substance 1) was used as a test substance. An unpulverized clarithromycin suspension (test substance 2) and a clarithromycin solution in DMSO (test substance 3) were used as controls for comparisons.

(2-1) Preparing Medium Containing Test Substances

Each of the test substances was stirred for 15 seconds or more using a vortex mixer before dilution. The clarithromycin-containing samples (test substances 1 to 3) were diluted with Mueller Hinton II broth to be a concentration of 250 µg/mL, and then two-fold diluted serially to prepare mediums containing the each sample at a final drug concentration of 0.012 to 25 µg/mL, which were used for inoculation of Staphylococcus aureus subsp. aureus. Similarly, the samples were diluted with Mueller Hinton II broth to a concentration of 1000 µg/mL, and then two-fold diluted serially to prepare mediums containing the each sample at a final drug concentration of 0.049 to 100 µg/mL, which were used for inoculating Pseudomonas aeruginosa.

To a U-shaped well microplate, 0.1±0.02 mL per well of the each prepared test substance-containing medium was dispensed. Drug-free medium was dispensed into two wells as a control.

(2-2) Preparation of Bacterium Liquid

Staphylococcus aureus subsp. aureus or Pseudomonas aeruginosa was cultured overnight in Mueller Hinton II agar medium. The fresh cultured bacterium on the agar plate was suspended in equivalent to 0.5 McFarand (about $10^8$ CFU/mL) with sterilized saline and further diluted tenfold (about $10^7$ CFU/mL) with sterilized saline to prepare a bacterium liquid.

(2-3) Inoculation and Culture of the Bacterium Liquid

To each of the wells to which the test substance-containing medium or the test substance-free medium was dispensed, 0.005 mL of the bacterium liquid of Staphylococcus aureus subsp. aureus or Pseudomonas aeruginosa prepared in the above (2-2) was inoculated (final amount of bacterium liquid: about $10^4$ CFU/well). The bacterium liquid was not inoculated to a part of the wells with the test substance-free medium to prepare negative control wells. After inoculation, the media were cultured at 35±1° C. for 18 to 24 hours.

(2-4) Determination

After confirming growth in the control wells containing the test substance-free media, the minimum inhibitory concentration (MIC) was determined as the minimum drug concentration in which the growth of bacterium was not detected with the naked eye. Specifically, when turbidity or a precipitation with a diameter of 1 mm or more was observed with the naked eye, or when two or more flocs were observed even when a precipitate had a diameter of 1 mm or less, the growth was determined positive (+). When turbidity or a precipitation was not observed with the naked eye, or when only one precipitation with the diameter of 1 mm or less was observed, the growth was determined negative (−).

(3) Results

The results are shown in Table 4. The obtained results suggest that nanoized clarithromycin has the antibacterial activity equivalent to unpulverized clarithromycin and dissolved clarithromycin.

TABLE 4

| | Minimum inhibitory concentration (µg/mL) | |
|---|---|---|
| Tested substance | Staphylococcus aureus subsp. aureus | Pseudomonas aeruginosa |
| Clarithromycin suspension prepared in Example 6 (1) | 0.391 | >100 |
| | 0.391 | >100 |
| | 0.391 | >100 |
| | 0.391 | >100 |
| | 0.391 | >100 |
| Unpulverized clarithromycin suspension | 0.391 | >100 |
| | 0.391 | >100 |
| | 0.391 | >100 |
| | 0.391 | >100 |
| | 0.391 | >100 |
| Clarithromycin solution in DMSO | 0.391 | >100 |
| | 0.391 | >100 |
| | 0.391 | >100 |
| | 0.391 | >100 |
| | 0.391 | >100 |

Example 7

Eye Irritation Test (1) Preparation of a Nanoized Clarithromycin Suspension Formulation (1-1) Pulverization of Clarithromycin To a 1 L TRI-MIX (INOUE MFG., INC.), 30.1 g of clarithromycin having an average particle diameter of 10,370 nm (melting point: 217 to 220° C.; Assia Chemical Industries Ltd.), 90.1 g of mannitol (Wako Pure Chemical Industries, Ltd.), 8.9 g of polyvinylpyrrolidone K25 (Wako Pure Chemical Industries, Ltd.), and 12.0 g of hydrogenated soybean lecithin PHOSPHOLIPON 90H (H. Holstein Co., Ltd.) were fed and homogeneously mixed, and then 21.5 g of glycerol was added thereto, which was pulverized at 5° C. for 5 hours with maintaining the content in the dough state. The obtained kneaded dough had a recovered amount of 136.6 g (yield 84%).

(1-2) Particle Diameter Distribution Measurement of Nanoized Clarithromycin

To 100 mg of the obtained kneaded dough, 3 g of 0.1% HCO-60 (Nihon Surfactant Kogyo K.K.) was added and dispersed for several minutes using a bathtub type ultrasonic disperser (VS-100III, AS ONE Corporation). As a result of measuring the particle diameter distributions of clarithromycin using a particle diameter distribution counter, the average particle diameter (Dv) was 159.7 nm.

(1-3) Preparation of a Nanoized Clarithromycin Suspension Formulation (Clarithromycin Concentration 0.3%)

After pulverization by the TRI-MIX A, 1.25 g of the clarithromycin kneaded product (kneaded dough) was weighed in a 50 mL-glass vial, to which 10 g of an aqueous 1% HCO-60 (Nihon Surfactant Kogyo K.K.) solution was added, and then dispersed for 1 to 2 minutes using a bathtub type ultrasonic disperser (VS-100III, AS ONE Corporation), followed by further dispersion for 1 minute using a probe-type ultrasonic disperser (S-4000, MISONIX). Subsequently, 10 g of an aqueous 1% HCO-60 solution, 17.5 g of an aqueous 1% HPMC (60SH-50) solution, 7.5 g of a 1M Tris buffer solution, and 0.75 g of an aqueous 0.1% benzalkonium chloride solution were added, and total amount was adjusted to be 75 g with purified water. The mixture was stirred for 30 minutes using a magnetic stirrer to obtain a nanoized clarithromycin suspension formulation (clarithromycin concentration 0.3%).

(1-4) Preparation of a Nanoized Clarithromycin Suspension Formulation (Clarithromycin Concentration 1.0%)

After pulverization in the TRI-MIX A, 4.05 g of the clarithromycin kneaded product (kneaded dough) was weighed in a beaker, to which 33.5 g of an aqueous 1% HCO-60 (Nihon Surfactant Kogyo K.K.) solution was added, and then dispersed for 1 to 2 minutes using a bathtub type ultrasonic disperser (VS-100III, AS ONE Corporation), followed by dispersion for 1 minute using a probe-type ultrasonic disperser (S-4000, MISONIX). Subsequently, 17.5 g of an aqueous 1% HPMC (60SH-50) solution, 7.5 g of a 1M Tris buffer solution, and 0.75 g of an aqueous 0.1% benzalkonium chloride solution were added, and total amount was adjusted to be 75 g with purified water. The mixture was stirred for 30 minutes using a magnetic stirrer to obtain a nanoized clarithromycin suspension formulation (clarithromycin concentration 1.0%).

(1-5) Preparation of a Clarithromycin Bulk Powder Suspension Formulation (Clarithromycin Concentration 1.0%)

In a beaker, 0.75 g of the clarithromycin was weighed, to which 33.5 g of an aqueous 1% HCO-60 (Nihon Surfactant Kogyo K.K.) solution was added, and then dispersed for 1 to 2 minutes using a bathtub type ultrasonic cdisperser (VS-100III, AS ONE Corporation), followed by further dispersion for 1 minute using a probe-type ultrasonic disperser (S-4000, MISONIX). Subsequently, 17.5 g of an aqueous 1% HPMC (60SH-50) solution, 7.5 g of a 1M Tris buffer solution, and 0.75 g of an aqueous 0.1% benzalkonium chloride solution were added, and total amount was adjusted to be 75 g with purified water. The mixture was stirred for 30 minutes using a magnetic stirrer to obtain a clarithromycin bulk powder suspension formulation (clarithromycin concentration 1.0%).

(2) Evaluation Test (2-1) The eye irritation is evaluated by administering (a) saline; (b) the nanoized clarithromycin suspension formulation (clarithromycin concentration 0.3%), (c) the nanoized clarithromycin suspension formulation (clarithromycin concentration 1.0%), or (d) the clarithromycin bulk powder suspension formulation (clarithromycin concentration 1.0%) produced in the above (1); or (e) AzaSite (registered trademark) (positive control) (azithromycin concentration 0.3%) to an eye of a rabbit at intervals of 30 minutes to several hours, once to 20 times a day, and subsequently applying fluoresceine to the eye to observe the corneal staining.

(2-2) To one eye of a rabbit, 50 µL of each of (b) the nanoized clarithromycin suspension formulation (clarithromycin concentration 0.3%) and (c) the nanoized clarithromycin suspension formulation (clarithromycin concentration 1.0%) produced in the above (1) were administered and the eye irritation was visually evaluated over a period of 6 hours. As a result, both of the (b) and (c) nanoized clarithromycin suspension formulations did not cause an increase in the number of blinking, bloodshot eyes, and a secretion, and the eye irritation was not recognized.

(2-3) Saline is administered to one eye of rabbits as a control, and the above formulations (b) to (e) is administered to the other eye at intervals of 30 minutes to several hours, once to 20 times a day, to evaluate the number of blinking and the eye irritation. For the eye irritation evaluation, the cornea, iris, and conjunctiva of both eyes are observed before administration and 1, 3, 5, and 24 hours later from the final administration, and the results are scored in accordance with the Draize's evaluation criteria.

The eye irritation of the nanoized clarithromycin suspension formulations is considered equivalent to or lower than the eye irritation of AzaSite, the positive control.

Example 8

Drug Efficacy Test on Infectious Animal Model (1) A corneal infection model is prepared by making cut in corneas of a white rabbit and subsequently inoculating *Pseudomonas aeruginosa* to the eye. After several hours from the bacterial inoculation, saline is applied to one eye of the rabbit and each of the formulations (b) to (e) prepared in Example 7 is applied to the other eye, once to 10 times a day for 3 to 5 days in both application. After several hours from the bacterial inoculation, infection symptoms of the external eyes are observed at every 24 hours for 4 to 8 days. The infection symptoms of the external eye are scored in accordance with the evaluation criteria of Hatano et al. and Nakamura et al. or the Draize's evaluation criteria.

(2) A corneal infection model is prepared by inoculating *Pseudomonas aeruginosa* in the conjunctival sac of a white rabbit. After confirming the development of keratitis (5 to 10 hours from the bacterial inoculation), saline is applied to one eye and each of the formulations (b) to (e) prepared in Example 7 is applied to the other eye, once to 10 times a day for 3 to 5 days in both application. After several hours from the bacterial inoculation, infection symptoms of the external eyes are observed at every 24 hours for 4 to 8 days. The infection symptoms of the external eye are scored in accordance with the evaluation criteria of Hatano et al. and Nakamura et al. or the Draize's evaluation criteria.

(3) A corneal infection model is prepared by making a cut in the cornea of a white rabbit and subsequently inoculating *Staphylococcus aureus* to the eye. Saline is applied to one eye of the rabbit and each of the formulations (b) to (e) prepared in Example 7 is applied to the other eye, once to 10 times a day for 3 to 5 days from several hours after the bacterial inoculation. After several hours from the bacterial inoculation, the infection symptoms of the external eyes are observed at every 24 hours for 4 to 8 days. The infection symptoms of the external eye were scored in accordance with the evaluation criteria of Hatano et al. and Nakamura et al. or the Draize's evaluation criteria.

(4) A corneal infection model is prepared by injecting *Staphylococcus aureus* into the cornea intraparenchymal of a white rabbit to create. Saline is applied to one eye of the rabbit and each of the formulations (b) to (e) prepared in Example 7 is applied to the other eye, once to 10 times a day for 3 to 5 days from several hours after the bacterial inoculation. After several hours from the bacterial inoculation, the infection symptoms of the external eyes are observed at every 24 hours for 4 to 8 days. The infection symptoms of the external eye were scored in accordance with the evaluation criteria of Hatano et al. and Nakamura et al. or the Draize's evaluation criteria.

The eye irritation (corneal opacity, palpebral conjunctival congestion, palpebral conjunctival edema, bulbar conjunctival congestion) of the nanoized clarithromycin suspension formulations from visual observation is considered to be equivalent to or lower than the eye irritation of AzaSite, the positive control. The antibacterial and antiinflammatory effects of the nanoized clarithromycin suspension formulations are considered equivalent to or higher than those of AzaSite, the positive control.

Example 9

Drug Efficacy Test on Inflammatory Animal Model (1) An acute conjunctival edema is created by injecting 2% arachidonic acid to the upper eyelid conjunctiva of a rat (conjunctivitis model). Before injecting the arachidonic acid, each of the formulations (a) to (e) prepared in Example 7 is applied to the eye once to several times every 15 to 30 minutes. The rats are killed 3 to 6 hours after the arachidonic acid injection, and the edema site is cut off along the border of eyelid to measure the weight thereof. The decrease ratio in the edema weight of the formulation-applied groups to the saline-applied group is calculated to evaluate the inhibitory effect on the conjunctival edema.
(2) An acute conjunctival edema is created by injecting 1% carrageenin to the upper eyelid conjunctiva of a rat (conjunctivitis model). Before injecting the carrageenin, each of the formulations (a) to (e) prepared in Example 7 is applied to the eye once to four times every 15 to 30 minutes. The rats are killed 3 to 6 hours after the carrageenin injection, and the edema site is cut off along the border of eyelid to measure the weight thereof. The decrease ratio in the edema weight of the formulation-applied groups to the saline-applied group is calculated to evaluate the inhibitory effect on the conjunctival edema.
(3) An acute conjunctival edema is created by injecting 1% carrageenin to the upper eyelid conjunctiva of a rat (conjunctivitis model). Immediately after the carrageenin injection, 1% Evans blue was administered via the tail vein. Before injecting carrageenin, each of the formulations (b) to (e) prepared in Example 7 is applied to one eye (right eye) and saline is applied to the other eye (left eye) once to four times every 15 to 30 minutes. The rats were killed 3 to 6 hours after the carrageenin injection and the eyelid skin is removed. The obtained eyelid skin is placed into a falcon tube, to which formamide is added, and then immersed in a refrigerator overnight. The dye content of Evans blue contained in the supernatant after centrifugation can be determined from an absorbance at 620 nm using a spectrophotometer. The inhibitory effect on conjunctival edema is evaluated as inhibition rate of dye leakage shown below.

Inhibition rate (%)={((dye leakage of left eye)−(dye leakage of right eye))/(dye leakage of left eye)}×100

(4) An acute conjunctival edema is created by injecting 1% formalin to the upper eyelid conjunctiva of a rat (conjunctivitis model). Before injecting the formalin, each of the formulations (a) to (e) prepared in Example 7 is applied to the eye once to four times every 15 to 30 minutes. The rats are killed 3 to 6 hours after the formalin injection, and the edema site is cut off along the border of eyelid to measure the weight thereof. The decrease ratio in the edema weight of the formulation-applied groups to the saline-applied group is calculated to evaluate the inhibitory effect on the conjunctival edema.
(5) An acute conjunctival edema is created by injecting 10% kaolin to the upper eyelid conjunctiva of a rat (conjunctivitis model). Before injecting the kaolin, each of the formulations (a) to (e) prepared in Example 7 is applied to the eye once to four times every 15 to 30 minutes. The rats are killed 3 to 6 hours after the kaolin injection, and the edema site is cut off along the border of eyelid to measure the weight thereof. The decrease ratio in the edema weight of the formulation-applied groups to the saline-applied group is calculated to evaluate the inhibitory effect on the conjunctival edema.
(6) An acute conjunctival edema is created by applying 10% croton oil to the conjunctival sac of a rat (conjunctivitis model). Before applying the croton oil, each of the formulations (a) to (e) prepared in Example 7 is applied to the eye once to four times every 30 to 50 minutes. The rats are killed 2 to 6 hours after the last croton oil application, and the edema site is cut off along the border of eyelid to measure the weight thereof. The decrease ratio in the edema weight of the formulation-applied groups to the saline-applied group is calculated to evaluate the inhibitory effect on the conjunctival edema.
(7) An uveitis is created by injecting bovine serum albumin to the vitreous humor of a rabbit (primary uveitis). After the inflammation is reduced (27 to 29 days after the bovine serum albumin injection to the vitreous humor), bovine serum albumin is injected again from the ear vein to recur the uveitis (secondary uveitis). Each of the formulations (a) to (e) prepared in Example 7 is applied to the primary uveitis and the secondary uveitis at intervals of 30 minutes to several hours, once to 6 times a day. The saline-applied group and the formulation-applied groups are observed for the inflammation symptoms of the external eye (corneal opacity, palpebral conjunctival congestion, palpebral conjunctival edema, bulbar conjunctival congestion) and for the inflammation symptoms of the internal eye (iris congestion, iris morphological changes, anterior chamber turbidity), which are scored in accordance with the scoring criteria in order to use as the uveitis indicator.

The visually observed eye irritation (corneal opacity, palpebral conjunctival congestion, palpebral conjunctival edema, bulbar conjunctival congestion) of the nanoized clarithromycin suspension formulations are considered equivalent to or lower than the eye irritation of AzaSite (registered trademark), the positive control. The anti-inflammatory effects of the nanoized clarithromycin suspension formulations are considered equivalent to or higher than those of AzaSite (registered trademark), the positive control.

Example 10

Stability Test of Nanoized Clarithromycin Suspension Formulation

A quantity of 6 to 8 g of the nanoized clarithromycin suspension formulations (clarithromycin concentrations 0.3% and 1.0%) produced in Example 7 (1) were weighed in a 9 mL-screw vial, allowed to stand in thermo-hygrostats each set at 5° C., 25° C., and 40° C. to carry out the stability test over a period of 14 days. On days 7 and 14, the clarithromycin concentrations were determined by high performance liquid chromatography (HPLC), and the residual ratio was determined as compared to the clarithromycin concentration immediately after the formulation which was taken as 100% to evaluate the stability. The HPLC analysis conditions were as follows.

Apparatus: Waters alliance
Column: Inertsil ODS 4.6 mm×150 mm
Column temperature: 50° C.
Eluate: 20 mM KH2PO4/CH3CN (8:2)
Detection wavelength: 210 nm The results of stability test are shown in Table 5. Clarithromycin was not decomposed but stable at each temperature of 5° C., 25° C. and 40° C. for all through the 14 days.

TABLE 5

|  | Clarithromycin concentration 0.3% | | | Clarithromycin concentration 1.0% | | |
| --- | --- | --- | --- | --- | --- | --- |
|  | 5° C. | 25° C. | 40° C. | 5° C. | 25° C. | 40° C. |
| Immediately after preparation (%) | 100 | 100 | 100 | 100 | 100 | 100 |
| Days 7 (%) | 100.0 | 99.8 | 100.8 | 100.0 | 100.4 | 99.4 |
| Days 14 (%) | 101.5 | 100.9 | 101.0 | 99.4 | 98.5 | 100.8 |

Example 11

Intraocular Kinetics Test of Nanoized Clarithromycin Suspension Formulations

Formulations of (b) the nanoized clarithromycin suspension formulation (clarithromycin concentration 0.3%), (c) the nanoized clarithromycin suspension formulation (clarithromycin concentration 1.0%), and (d) the clarithromycin bulk powder suspension formulation (clarithromycin concentration 1.0%) produced in Example 7 (1), or (e) AzaSite (registered trademark) (positive control) (azithromycin concentration 0.3%) are respectively applied to the eye of rabbits once to 10 times at intervals of 5 to 30 minutes, and the clarithromycin concentrations in the external eye tissues (conjunctiva, cornea, aqueous humor) after 30 minutes, 1, 2, 4, and 6 hours after the application are measured by HPLC or LC/MS/MS, etc.

The clarithromycin concentrations of the nanoized clarithromycin suspension formulations in the conjunctiva, cornea, and aqueous humor are considered to be higher than the clarithromycin bulk powder suspension formulation, and are considered equivalent to or higher than those of AzaSite, the positive control.

Example 12

Production of Pulverized Clarithromycin Dough

To a 0.5 L TRI-MIX (INOUE MFG., INC.), 30 g of clarithromycin having an average particle diameter of 10,370 nm (melting point: 217 to 220° C.; Assia Chemical Industries Ltd.), 90 g of mannitol (Wako Pure Chemical Industries, Ltd.), 9 g of polyvinylpyrrolidone K25 (Wako Pure Chemical Industries, Ltd.), and 12 g of hydrogenated soybean lecithin PHOSPHOLIPON 90H (H. Holstein Co., Ltd.) were fed and homogeneously mixed, and then 23.6 g of glycerol was added thereto, which was pulverized at 10° C. for 6 hours with maintaining the content in the dough state. The obtained kneaded dough had a recovered amount of 145.8 g (yield 88.5%).

To 100 mg of the obtained kneaded dough, 3 g of 0.1% HCO-60 (Nihon Surfactant Kogyo K.K.) was added and dispersed for several minutes in a bathtub type ultrasonic disperser (VS-100III, AS ONE Corporation). As a result of measuring the particle diameter distributions of clarithromycin using a particle diameter distribution counter, the average particle diameter (Dv) was 146.8 nm, the 10% diameter (D10) was 85.5 nm, the 50% diameter (D50) was 131.1 nm, and the 90% diameter (D90) was 222.0 nm.

Example 13

Production of Pulverized Azithromycin Dough

To a 0.5 L TRI-MIX (INOUE MFG., INC.), 5 g of azithromycin dihydrate having an average particle diameter of 74.99 μm (melting point: 133 to 135° C.; Tokyo Chemical Industry Co., Ltd.), 60 g of sodium chloride (Tomita Salt K30, Tomita Pharmaceutical Co., Ltd.), 8 g of a mixture of hydrogenated soybean lecithin (PHOSPHOLIPON 90H, H. Holstein Co., Ltd.)/glycerol (Junsei Chemical Co., Ltd.) (1:3), and 9.6 g of glycerol were fed, which was pulverized at 5° C. for 2 hours with maintaining the content in the dough state. The obtained kneaded dough had a recovered amount of 74.8 g (yield 90.6%).

To 100 mg of the obtained kneaded dough, 5 g of a mixed solution of 0.05% MYS-40 (Nihon Surfactant Kogyo K.K.)/ 0.05% PLONON 407P (Nippon Yushi Industry Co., Ltd.) was added and dispersed for several minutes using a bathtub type ultrasonic disperser (VS-100III, AS ONE Corporation), to which 45 g of purified water was added, and then the content was dispersed for several minutes using a bathtub-type ultrasonic disperser. As a result of measuring the particle diameter distributions of azithromycin using a particle diameter distribution counter, the average particle diameter (Dv) was 147.3 nm, the 10% diameter (D10) was 88.9 nm, the 50% diameter (D50) was 130.1 nm, and the 90% diameter (D90) was 188.2 nm.

Example 14

Production of Pulverized Roxithromycin Dough

To a 0.5 L TRI-MIX (INOUE MFG., INC.), 5 g of roxithromycin having an average particle diameter of 121.3 μm (melting point: 122 to 126° C.; Wako Pure Chemical Industry Co., Ltd.), 60 g of sodium chloride (Oshio micron T-0, AKO KASEI CO., LTD.), 8 g of a mixture of hydrogenated soybean lecithin (PHOSPHOLIPON 90H, H. Holstein Co., Ltd.)/glycerol (Junsei Chemical Co., Ltd.) (1:3), and 9.6 g of glycerol were fed, which were pulverized at 5° C. for 2 hours with maintaining the content in the dough state. The obtained kneaded dough had a recovered amount of 81.6 g (yield 98.4%).

To 100 mg of the obtained kneaded dough, 5 g of a mixed solution of 0.05% MYS-40 (Nihon Surfactant Kogyo K.K.)/ 0.05% PLONON 407P (Nippon Yushi Industry Co., Ltd.) was added and dispersed for several minutes using a bathtub type ultrasonic disperser (VS-100III, AS ONE Corporation), to which 25 g of purified water was added, and then the content was dispersed for several minutes using a bathtub-type ultrasonic disperser. As a result of measuring the particle diameter distributions of roxithromycin using a particle diameter distribution counter, the average particle diameter (Dv) was 234.5 nm, the 10% diameter (D10) was 119.0 nm, the 50% diameter (D50) was 195.0 nm, and the 90% diameter (D90) was 341.5 nm.

Example 15

Production of a 0.3% Nanoized Clarithromycin Suspension Formulation

After pulverization by the TRI-MIX in Example 12, 2.55 g of the clarithromycin kneaded product (kneaded dough) was weighed in a 50 mL-glass vial, to which 20.0 g of an aqueous 1% HCO-60 solution was added and dispersed for 1 to 2 minutes using a bathtub type ultrasonic disperser (VS-100III, AS ONE Corporation), followed by further dispersion for 1 minute (30 seconds×2) using a probe-type ultrasonic disperser (S-4000, MISONIX). As a result of measuring the particle diameter distributions of clarithromycin in the dispersion using a particle diameter distribution counter, the average particle diameter (Dv) was 219.2 nm.

To the above obtained dispersion, 20.0 g of an aqueous 1% HCO-60 solution, 35.0 g of an aqueous 1% HPMC 60SH-50 solution, 15.0 g of 1M Tris buffer solution (pH 7.5), and 1.5 g of an aqueous 0.1% benzalkonium chloride (BAC) solution were added and stirred using a magnetic stirrer, which was adjusted to be 150 g with purified water, followed by stirring and mixing to produce the 0.3% formulation. As a result of measuring the particle diameter distributions of clarithromycin in the formulation using a particle diameter distribution counter, the average particle diameter (Dv) was 391.9 nm, the 10% diameter (D10) was 205.3 nm, the 50% diameter (D50) was 326.1 nm, and the 90% diameter (D90) was 556.5 nm.

Example 16

Production of a 1.0% Nanoized Clarithromycin Suspension Formulation

After pulverization by the TRI-MIX in Example 12, 5.55 g of the clarithromycin kneaded product (kneaded dough) was weighed in a glass beaker, to which 46.7 g of an aqueous 1% HCO-60 solution was added and dispersed for 1 to 2 minutes using a bathtub type ultrasonic disperser (VS-100III, AS ONE Corporation), followed by dispersion for 1 minute (30 seconds×2) using a probe-type ultrasonic disperser (S-4000, MISONIX). As a result of measuring the particle diameter distributions of clarithromycin in the dispersion using a particle diameter distribution counter, the average particle diameter (Dv) was 217.6 nm.

To the above dispersion, 23.3 g of an aqueous 1% HPMC 60SH-50 solution, 7.5 g of a 1M Tris buffer solution (pH 7.5), and 1.0 g of an aqueous 0.1% benzalkonium chloride (BAC) solution were added and stirred using a magnetic stirrer, which was adjusted to be 100 g with purified water, followed by stirring and mixing to produce the 1.0% formulation. As a result of measuring the particle diameter distributions of clarithromycin in the formulation, the average particle diameter (Dv) was 548.1 nm, the 10% diameter (D10) was 294.4 nm, the 50% diameter (D50) was 484.4 nm, and the 90% diameter (D90) was 785.6 nm.

Example 17

Intraocular Pharmacokinetics Test of Nanoized Clarithromycin Suspension Formulations The intraocular pharmacokinetics test was carried out as described below using three kinds of formulations, the 0.3% nanoized clarithromycin suspension formulation produced in Example 15 (hereinafter referred to as the 0.3% nanoized formulation), the 1.0% nanoized clarithromycin suspension formulation produced in Example 16 (hereinafter referred to as the 1.0% nanoized formulation), and the 1.0% clarithromycin bulk powder suspension formulation (hereinafter referred to as the 1.0% bulk powder formulation).

The lower eyelid of a rabbit (strain Kbl: JW, male) was gently pulled off, 50 μL each of the formulations was applied once to the conjunctival sac of the left eye using a pipette, and subsequently the upper and lower eyelids were gently closed and held for about 2 seconds. At 30 minutes, 2, 4, and 6 hours after the application to the eye, the plasma, aqueous humor, and conjunctiva were collected to measure the clarithromycin concentrations by LC-MS/MS.

The plasma was collected as follows. About 1 mL of blood was collected from the auricular vein and quickly centrifuged (4° C., 1710×g, 3000 rpm) to obtain the plasma. The obtained plasma was cryopreserved in a ultra-deep freezer (−70° C. or less) until analyzed.

The aqueous humor and conjunctiva were collected as follows. After the blood collection, the rabbit was anesthetized by intravenously administering a pentobarbital aqueous solution to the auricle, and then euthanized by bleeding. After thoroughly washing the eye with water for injection, the aqueous humor was collected, and then the conjunctiva was collected. Each of the collected aqueous humor and conjunctiva were weighed and frozen in liquid nitrogen, and cryopreserved in a ultra-deep freezer (−70° C. or less) until analyzed.

Pretreatments of each sample were carried out as follows. For the plasma, 50 μL of acetonitrile was added to 20 μL of the plasma, which was thoroughly stirred and then centrifuged (13100×g, 4° C., 5 minutes), and 2 μL of the supernatant was injected for LC-MS/MS. For the aqueous humor, 50 μL of acetonitrile was added to 20 μL of the aqueous humor, which was thoroughly stirred and then centrifuged (13100×g, 4° C., 5 minutes), and 2 μL of the supernatant was injected for LC-MS/MS. For the conjunctiva, after addition of ultrapure water of 9 times as much volume as a wet weight of the conjunctiva to the conjunctiva, the conjunctiva was homogenized. To 20 μL of the conjunctival homogenate, 50 μL of acetonitrile was added, which was thoroughly stirred and then centrifuged (13100×g, 4° C., 5 minutes), and 2 μL of the supernatant was injected for LC-MS/MS.

The HPLC analysis conditions were as follows:

| Column | Inertsil ODS-4 HP (GL Sciences) | |
|---|---|---|
| Mobile phase A | 20 mM Ammonium formate | |
| Mobile phase B | Acetonitrile | |
| | Time (min) | Mobile phase A (%) | Mobile phase B (%) |
| Gradient | | | |
| | 0.00 | 60 | 40 |
| | 3.00 | 20 | 80 |
| | 4.50 | 20 | 80 |
| | 4.51 | 60 | 40 |
| | 6.00 | 60 | 40 |

-continued

| | |
|---|---|
| Flow rate | 0.2 mL/min |
| Column temperature | 40° C. |
| Auto sampler temperature | 4° C. |
| Amount dosed | 2 μL |
| Analysis time | 6 minutes |

The MS/MS analysis conditions were as follows:

| | | | |
|---|---|---|---|
| Ion Source: | Electrospray ionization (ESI) | | |
| Scan Type: | Multiple reaction monitoring (MRM) | | |
| Polarity: | Positive | | |
| Source Temperature: | 500° C. | | |
| Monitor ion: | Compound | Q1 (m/z) | Q3 (m/z) |
| | Clarithromycin | 749.00 | 158.00 |

The results are shown in FIGS. 1 to 3. As compared to the bulk powder, the nanoized clarithromycin have higher migration properties to the aqueous humor and conjunctiva, and substantially equal migration properties to blood.

Example 18

Efficacy Test of Nanoized Clarithromycin Suspension Formulations 1

A corneal ulcer model was created in a rabbit, and conjunctivitis was developed by *Staphylococcus aureus* infection in order to evaluate the effectiveness of the nanoized clarithromycin suspension formulations (eye drops) as follows.

The corneal ulcer model was created as follows. The external eye of a Japanese white color species rabbit (strain Slc: JW/CSK, male) was washed with saline under pentobarbital sodium anesthesia (intravenously administering to the auricle), and the cornea was locally anesthetized with 0.4% oxybuprocaine hydrochloride. An eyeball of the rabbit was dislocated by compression using a dispensing spoon, a shallow circular cut was made in the center of the cornea by a 6 mm-diameter trephine (Castroviejo corneal transplant trephine), and a "#" sign-shaped cut with two pairs of vertical and horizontal parallel lines reaching the cornea intraparenchymal was made inside the circular cut using a 26 G×½ SB needle.

The bacterium liquid was inoculated as follows. A bacterium liquid of *Staphylococcus aureus* (St. *aureus* ATCC25923 strain) in a concentration of $1 \times 10^9$ cfu/mL was instilled once to the cornea at 50 μL/eye using a micropipette and a chip. The rabbit was allowed to blink, and the eyelid was gently massaged a few times. The bacterium liquid was dropped one more time, the rabbit was allowed to blink, and the eyelid was gently massaged a few times (0.1 mL per eye was instilled onto the cornea).

Test substances were AzaSite (1% azithromycin ophthalmic solution), the 0.3% nanoized clarithromycin formulation produced in Example 15, the 1.0% nanoized clarithromycin formulation produced in Example 16, and the 1.0% clarithromycin bulk powder suspension formulation, and a vehicle (the same composition with the above 0.3% nanoized clarithromycin formulation except that clarithromycin was not contained).

The test substances were administered as follows. The lower eyelid was gently pulled off and 50 μL/eye of the test substance was instilled in the conjunctival sac using a micropipette and a chip. The test substance was administered for four days, twice (4 hours and 8 hours after the bacterium liquid inoculation) on the day of bacterium liquid inoculation (day 1) and three times a day (a 4 hour interval) on days 2 to 4.

TABLE 6

| Group | Bacterium liquid concentration (cfu/cornea) | Tested sample | Treatment | Number of eyes/number of animals |
|---|---|---|---|---|
| 1 | $1 \times 10^8$ | Vehicle | twice per day for Day 1 three times per day for Days 2 to 4 | 4/4 |
| 2 | | AzaSite | | 4/4 |
| 3 | | 0.3% nanoized clarithromycin | | 4/4 |
| 4 | | 1.0% nanoized clarithromycin | | 4/4 |
| 5 | | 1.0% clarithromycin bulk powder | | 4/4 |

The result was observed and drug efficacy was evaluated and determined as follows. The corneal infection site, cornea, iris, and conjunctiva were observed once a day for 7 days from day 1 to day 7 after the bacterium liquid inoculation using a slit lamp microscopy. For the drug efficacy evaluation and determination, the evaluation of corneal findings in accordance with the evaluation criteria by Hatano et al. and Nakamura et al. (Table 7), and the evaluations of corneal, iridic, and conjunctival findings in accordance with the evaluation criteria of Draize J. H. et. al. (Table 8) were employed. The evaluation utilizing the evaluation criteria of Draize J. H. et. al. was carried out as follows:

Cornea=$A \times B \times 5$ (Maximum 80 points)

Iris=×5 (Maximum 10 points)

Conjunctiva=$(A+B+C) \times 2$ (Maximum 20 points)

Total score=cornea+iris+conjunctiva (Maximum 110 points)

TABLE 7

The evaluation criteria by Hatano et al. and Nakamura et al.

| Region | Observation image | Evaluation |
|---|---|---|
| Cornea | Area of corneal turbidity | |
| | No corneal turbidity | 0 |
| | No corneal turbidity but light edema | 0.5 |
| | Corneal turbidity smaller than 6 mm | +1 |
| | Corneal turbidity whole of 6 mm | +2 |
| | Corneal turbidity larger than 6 mm | +3 |
| | Corneal turbidity whole of cornea | +4 |

TABLE 8

The evaluation criteria by Draize J. H. et. al.

| Region | Degree of eye response | Evaluation |
|---|---|---|
| Cornea | (A) Degree of density (area which is most dense is taken for reading) | |
| | Clear - No density | 0 |
| | Scattered or diffuse area - details of iris clearly visible | +1 |
| | Easily discernible translucent areas, details of iris slightly obscured | +2 |
| | Opalescent areas, no details of iris visible, size of pupil barely discernible | +3 |
| | Opaque, iris invisible | +4 |
| | (B) Area of cornea involved | |
| | 0 | 0 |
| | 0 < Area < ¼ | +1 |
| | ¼ ≤ Area < ½ | +2 |
| | ½ ≤ Area < ¾ | +3 |
| | ¾ ≤ Area < 4/4 | +4 |
| Iris | Normal | 0 |
| | Folds above normal, congestion, swelling, circumcorneal injection (any one or all of these or combination of any thereof), iris still reacting to light (sluggish reaction is positive) | +1 |
| | No reaction to light, hemorrhage, gross destruction (any one of these) | +2 |
| Conjunctiva | (A) Redness (refers to palpebral conjunctiva and bulbar conjunctiva) | |
| | Vessels are normal | 0 |
| | Vessels definitely injected above normal | +1 |
| | More dissuse, deeper crimson red, individual vessels not easily discernible | +2 |
| | Diffuse beefy red | +3 |
| | (B) Chemosis | |
| | No swelling | 0 |
| | Any swelling above normal (includes nictitating membrane) | +1 |
| | Obvious swelling with partial eversion of the lids | +2 |
| | Swelling with lids about half closed | +3 |
| | Swelling with lids about half closed to completely closed | +4 |
| | (C) Discharge | |
| | No discharge | 0 |
| | Any amount different from normal | +1 |
| | Discharge with moistening of the lids and hairs just adjacent to the lids | +2 |
| | Discharge with moistening of the lids and considerable area around the eye | +3 |

Table 9 collectively shows the score results of the corneal infection sites based on the evaluation criteria of Hatano et al. and Nakamura et al. FIG. 4 shows the over-time changes of the score in each of the test substances (drug efficacy evaluations).

TABLE 9

| Group | Animal number | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| 1 | M02101 | 1 | 1 | 1 | 1 | 4 | 4 | 4 |
| | M02102 | 2 | 2 | 2 | 2 | 2 | 1 | 1 |
| | M02103 | 2 | 2 | 1 | 1 | 1 | 4 | 4 |
| | M02104 | 3 | 3 | 3 | 3 | 2 | 1 | 1 |
| | Mean | 2.00 | 2.00 | 1.75 | 1.75 | 2.25 | 2.50 | 2.50 |
| | S.E. | 0.41 | 0.41 | 0.48 | 0.48 | 0.63 | 0.87 | 0.87 |
| 2 | M03101 | 1 | 1 | 1 | 1 | 1 | 1 | 1 |
| | M03102 | 1 | 1 | 1 | 1 | 1 | 1 | 0 |
| | M03103 | 1 | 1 | 1 | 1 | 1 | 1 | 1 |
| | M03104 | 0 | 0 | 1 | 1 | 1 | 1 | 1 |
| | Mean | 0.75 | 0.75 | 1.00 | 1.00 | 1.00 | 1.00 | 0.75 |
| | S.E. | 0.25 | 0.25 | 0.00 | 0.00 | 0.00 | 0.00 | 0.25 |
| 3 | M04101 | 1 | 0 | 0 | 0 | 0 | 0 | 0 |
| | M04102 | 0 | 0 | 0 | 0 | 0 | 0 | 0 |
| | M04103 | 1 | 1 | 1 | 1 | 1 | 1 | 1 |
| | M04104 | 1 | 0 | 0 | 0 | 0 | 0 | 0 |
| | Mean | 0.75 | 0.25 | 0.25 | 0.25 | 0.25 | 0.25 | 0.25 |
| | S.E. | 0.25 | 0.25 | 0.25 | 0.25 | 0.25 | 0.25 | 0.25 |
| 4 | M05101 | 0 | 0 | 0 | 0 | 0 | 0 | 0 |
| | M05102 | 2 | 1 | 1 | 1 | 1 | 1 | 1 |
| | M05103 | 0 | 0 | 0 | 0 | 0 | 0 | 0 |
| | M05104 | 0 | 0 | 0 | 0 | 0 | 0 | 0 |
| | Mean | 0.50 | 0.25 | 0.25 | 0.25 | 0.25 | 0.25 | 0.25 |
| | S.E. | 0.50 | 0.25 | 0.25 | 0.25 | 0.25 | 0.25 | 0.25 |
| 5 | M06101 | 0 | 0 | 0 | 0 | 0 | 0 | 2 |
| | M06102 | 0 | 0 | 0 | 0 | 0 | 0 | 2 |
| | M06103 | 1 | 0 | 0 | 0 | 0 | 0 | 0 |

TABLE 9-continued

| Group | Animal number | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| | M06104 | 0 | 0 | 0 | 0 | 0 | 0 | 0 |
| | Mean | 0.25 | 0.00 | 0.00 | 0.00 | 0.00 | 0.00 | 1.00 |
| | S.E. | 0.25 | 0.00 | 0.00 | 0.00 | 0.00 | 0.00 | 0.58 |

Table 10 collectively shows the score results of the corneal, iridic, and conjunctival infection sites based on the evaluation criteria of Draize et al. FIG. 5 shows the over-time changes of the score in each of the test substances (drug efficacy evaluations).

TABLE 10

| Group | Animal number | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| 1 | M02101 | 20 | 20 | 20 | 20 | 81 | 81 | 81 |
| | M02102 | 35 | 35 | 35 | 33 | 27 | 22 | 20 |
| | M02103 | 27 | 27 | 22 | 24 | 24 | 83 | 88 |
| | M02104 | 53 | 49 | 49 | 49 | 27 | 20 | 20 |
| | Mean | 33.75 | 32.75 | 31.50 | 31.50 | 39.75 | 51.50 | 52.25 |
| | S.E. | 7.11 | 6.22 | 6.71 | 6.44 | 13.77 | 17.62 | 18.67 |
| 2 | M03101 | 15 | 18 | 18 | 18 | 22 | 24 | 24 |
| | M03102 | 20 | 20 | 18 | 16 | 16 | 14 | 2 |
| | M03103 | 13 | 11 | 18 | 18 | 16 | 16 | 14 |
| | M03104 | 13 | 13 | 18 | 18 | 18 | 18 | 18 |
| | Mean | 15.25 | 15.50 | 18.00 | 17.50 | 18.00 | 18.00 | 14.50 |
| | S.E. | 1.65 | 2.10 | 0.00 | 0.50 | 1.41 | 2.16 | 4.65 |
| 3 | M04101 | 26 | 15 | 8 | 6 | 6 | 2 | 0 |
| | M04102 | 19 | 19 | 17 | 8 | 8 | 6 | 2 |
| | M04103 | 20 | 18 | 22 | 20 | 22 | 26 | 28 |
| | M04104 | 22 | 11 | 13 | 6 | 6 | 6 | 2 |
| | Mean | 21.75 | 15.75 | 15.00 | 10.00 | 10.50 | 10.00 | 8.00 |
| | S.E. | 1.55 | 1.80 | 2.97 | 3.37 | 3.86 | 5.42 | 6.68 |
| 4 | M05101 | 13 | 9 | 11 | 11 | 4 | 4 | 2 |
| | M05102 | 25 | 18 | 16 | 16 | 9 | 9 | 9 |
| | M05103 | 10 | 6 | 4 | 0 | 0 | 0 | 0 |
| | M05104 | 15 | 13 | 13 | 8 | 6 | 6 | 6 |
| | Mean | 15.75 | 11.50 | 11.00 | 8.75 | 4.75 | 4.75 | 4.25 |
| | S.E. | 3.25 | 2.60 | 2.55 | 3.35 | 1.89 | 1.89 | 2.02 |
| 5 | M06101 | 15 | 11 | 6 | 6 | 8 | 21 | 37 |
| | M06102 | 8 | 6 | 6 | 6 | 6 | 4 | 43 |
| | M06103 | 22 | 11 | 11 | 11 | 9 | 9 | 9 |
| | M06104 | 12 | 10 | 8 | 6 | 6 | 4 | 4 |
| | Mean | 14.25 | 9.50 | 7.75 | 7.25 | 7.25 | 9.50 | 23.25 |
| | S.E. | 2.95 | 1.19 | 1.18 | 1.25 | 0.75 | 4.01 | 9.80 |

FIGS. 4 and 5 revealed that the anti-inflammatory effects of the nanoized clarithromycin suspensions (eye drops) are equivalent to or more than those of AzaSite, the positive control. The 1.0% clarithromycin bulk powder formulation exhibited attenuated anti-inflammatory effects from day 6, whereas the nanoized clarithromycin suspensions (eye drops) maintained the anti-inflammatory effects over a period of 7 days. Consequently, it is verified that the nanoization enables the drug efficacy to last longer term than the bulk powder.

Example 19

Efficacy Test of Nanoized Clarithromycin Suspension Formulations 2

A corneal ulcer model was created using a rabbit, and conjunctivitis was caused to develop by *Staphylococcus aureus* infection in order to evaluate the drug efficacy of the nanoized clarithromycin suspension formulations (eye drops). In this example, the therapeutic effects of delayed initial eye drop administration was studies as compared with Example 18.

The creation of a corneal ulcer model, the inoculation of the bacterium liquid, and drug efficacy evaluation and determination were carried out in the same manner as in Example 18. The test substances used were the 0.3% nanoized clarithromycin formulation produced in Example 15 and a vehicle (the same composition as the 0.3% nanoized clarithromycin formulation except that clarithromycin was not contained). The number of administration, etc. are collectively shown in Table below.

TABLE 11

| Group | Bacterium liquid concentration (cfu/cornea) | Tested sample | Treatment | Number of eyes/number of animals |
|---|---|---|---|---|
| 1 | $1 \times 10^8$ | No treatment group | None | 10/5 |
| 2 | | Vehicle | 10 hours after inoculation, 5 times per day for 3 days | 10/5 |
| 3 | | 0.3% nanoized | 4 hours after inoculation, | 10/5 |

TABLE 11-continued

| Group | Bacterium liquid concentration (cfu/cornea) | Tested sample | Treatment | Number of eyes/number of animals |
|---|---|---|---|---|
| 4 | | clarithromycin | 2 times per day for Day 1 and 3 times per day for Days 2 and 3 10 hours after inoculation, 3 times per day for 3 days | 10/5 |
| 5 | | | 10 hours after inoculation, 5 times per day for 3 days | 10/5 |

Tables 12 and 13 collectively show the score results of the corneal infection sites based on the evaluation criteria of Hatano et al. and Nakamura et al. FIG. 6 shows the over-time changes of the score in each of the test substances (drug efficacy evaluations).

TABLE 12

| Group | Region | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| 1 | Left eye | 1 | 2 | 1 | 1 | 1 | 1 | 1 |
|   | Right eye | 2 | 1 | 2 | 2 | 2 | 1 | 3 |
|   | Left eye | 1 | 1 | 1 | 1 | 1 | 4 | 4 |
|   | Right eye | 1 | 1 | 1 | 1 | 1 | 1 | 0 |
|   | Left eye | 1 | 1 | 1 | 1 | 1 | 1 | 0 |
|   | Right eye | 1 | 1 | 1 | 1 | 1 | 0.5 | 0.5 |
|   | Left eye | 1 | 0 | 0 | 0 | 0 | 0 | 0 |
|   | Right eye | 1 | 1 | 1 | 1 | 0 | 0 | 0 |
|   | Left eye | 1 | 1 | 0 | 0 | 0 | 0 | 0 |
|   | Right eye | 1 | 1 | 1 | 1 | 1 | 0 | 0 |
|   | Mean | 1.10 | 1.00 | 0.90 | 0.90 | 0.80 | 0.85 | 0.85 |
|   | S.E. | 0.10 | 0.15 | 0.18 | 0.18 | 0.20 | 0.38 | 0.46 |
| 2 | Right eye | 1 | 1 | 1 | 1 | 1 | 1 | 0 |
|   | Left eye | 2 | 2 | 1 | 1 | 1 | 1 | 1 |
|   | Right eye | 1 | 1 | 1 | 1 | 0 | 0 | 0 |
|   | Left eye | 1 | 1 | 1 | 1 | 1 | 1 | 1 |
|   | Right eye | 1 | 0 | 0 | 0 | 0 | 0 | 0 |
|   | Left eye | 0.5 | 0 | 0 | 0 | 0 | 0 | 0 |
|   | Right eye | 1 | 1 | 1 | 1 | 1 | 2 | 2 |
|   | Left eye | 1 | 2 | 2 | 1 | 1 | 0 | 0 |
|   | Right eye | 1 | 0.5 | 0.5 | 0 | 0 | 0 | 0 |
|   | Left eye | 1 | 1 | 1 | 1 | 1 | 1 | 1 |
|   | Mean | 1.05 | 0.95 | 0.85 | 0.70 | 0.60 | 0.60 | 0.50 |
|   | S.E. | 0.12 | 0.22 | 0.18 | 0.15 | 0.16 | 0.22 | 0.22 |
| 3 | Left eye | 1 | 1 | 1 | 0 | 0 | 0 | 0 |
|   | Right eye | 1 | 1 | 1 | 1 | 1 | 1 | 0.5 |
|   | Left eye | 1 | 1 | 1 | 0 | 0 | 0 | 0 |
|   | Right eye | 1 | 1 | 1 | 1 | 0 | 0 | 0 |
|   | Left eye | 1 | 1 | 1 | 1 | 1 | 0.5 | 0 |
|   | Right eye | 1 | 0 | 0 | 0 | 0 | 0 | 0 |
|   | Left eye | 1 | 1 | 1 | 1 | 1 | 1 | 0 |
|   | Right eye | 0.5 | 0 | 0 | 0 | 0 | 0 | 0 |
|   | Left eye | 1 | 1 | 1 | 1 | 1 | 1 | 1 |
|   | Right eye | 1 | 0 | 0 | 0 | 0 | 0 | 0 |
|   | Mean | 0.95 | 0.70 | 0.70 | 0.50 | 0.40 | 0.35 | 0.15 |
|   | S.E. | 0.05 | 0.15 | 0.15 | 0.17 | 0.16 | 0.15 | 0.11 |

TABLE 13

| Group | Region | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| 4 | Right eye | 1 | 0 | 0 | 0 | 0 | 0 | 0 |
|   | Left eye | 2 | 2 | 2 | 2 | 1 | 1 | 1 |
|   | Right eye | 1 | 1 | 1 | 1 | 1 | 1 | 0.5 |
|   | Left eye | 1 | 1 | 1 | 0.5 | 0 | 0 | 0 |
|   | Right eye | 1 | 1 | 1 | 1 | 1 | 1 | 1 |
|   | Left eye | 1 | 0 | 0 | 0 | 0 | 0 | 0 |
|   | Right eye | 1 | 1 | 1 | 1 | 1 | 0 | 0 |
|   | Left eye | 1 | 1 | 1 | 0.5 | 0.5 | 0 | 0 |
|   | Right eye | 1 | 0 | 0 | 0 | 0 | 0 | 0 |
|   | Left eye | 0.5 | 0 | 0 | 0 | 0 | 0 | 0 |
|   | Mean | 1.05 | 0.70 | 0.70 | 0.60 | 0.45 | 0.30 | 0.25 |
|   | S.E. | 0.12 | 0.21 | 0.21 | 0.21 | 0.16 | 0.15 | 0.13 |
| 5 | Left eye | 1 | 0 | 0 | 0 | 0 | 0 | 0 |
|   | Right eye | 1 | 1 | 1 | 1 | 0 | 0 | 0 |

TABLE 13-continued

| Group | Region | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| | Left eye | 2 | 1 | 1 | 1 | 0 | 0 | 0 |
| | Right eye | 1 | 1 | 1 | 0 | 0 | 0 | 0 |
| | Left eye | 0.5 | 0 | 0 | 0 | 0 | 0 | 0 |
| | Right eye | 2 | 0 | 0 | 0 | 0 | 0 | 0 |
| | Left eye | 1 | 0 | 0 | 0 | 0 | 0 | 0 |
| | Right eye | 1 | 0.5 | 0 | 0 | 0 | 0 | 0 |
| | Left eye | 1 | 1 | 1 | 1 | 0 | 0 | 0 |
| | Right eye | 1 | 0 | 0 | 0 | 0 | 0 | 0 |
| | Mean | 1.15 | 0.45 | 0.40 | 0.30 | 0.00 | 0.00 | 0.00 |
| | S.E. | 0.15 | 0.16 | 0.16 | 0.15 | 0.00 | 0.00 | 0.00 |

Tables 14 and 15 collectively show the score results of the corneal, iridic, and conjunctival infection sites based on the evaluation criteria of Draize et al. FIG. 7 shows the over-time changes of the score in each of the test substances (drug efficacy evaluations).

TABLE 14

| Group | Region | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| 1 | Left eye | 30 | 39 | 24 | 18 | 18 | 18 | 18 |
| | Right eye | 45 | 22 | 37 | 35 | 33 | 18 | 47 |
| | Left eye | 26 | 24 | 22 | 18 | 30 | 85 | 90 |
| | Right eye | 26 | 24 | 18 | 18 | 20 | 18 | 8 |
| | Left eye | 26 | 20 | 18 | 16 | 16 | 18 | 8 |
| | Right eye | 24 | 20 | 22 | 20 | 18 | 8 | 8 |
| | Left eye | 24 | 8 | 6 | 6 | 11 | 11 | 13 |
| | Right eye | 24 | 18 | 16 | 18 | 6 | 6 | 8 |
| | Left eye | 22 | 20 | 6 | 6 | 4 | 4 | 8 |
| | Right eye | 22 | 16 | 18 | 16 | 16 | 6 | 10 |
| | Mean | 26.90 | 21.10 | 18.70 | 17.10 | 17.20 | 19.20 | 21.80 |
| | S.E. | 2.14 | 2.47 | 2.82 | 2.54 | 2.91 | 7.53 | 8.48 |
| 2 | Right eye | 26 | 24 | 20 | 16 | 16 | 14 | 8 |
| | Left eye | 31 | 43 | 22 | 16 | 16 | 16 | 16 |
| | Right eye | 26 | 24 | 20 | 16 | 11 | 11 | 6 |
| | Left eye | 22 | 22 | 18 | 16 | 16 | 16 | 16 |
| | Right eye | 22 | 10 | 6 | 2 | 6 | 8 | 8 |
| | Left eye | 13 | 6 | 8 | 2 | 2 | 2 | 2 |
| | Right eye | 28 | 26 | 18 | 24 | 24 | 39 | 43 |
| | Left eye | 26 | 29 | 27 | 16 | 16 | 9 | 9 |
| | Right eye | 28 | 15 | 8 | 4 | 4 | 4 | 4 |
| | Left eye | 24 | 22 | 22 | 16 | 22 | 20 | 18 |
| | Mean | 24.60 | 22.10 | 16.90 | 12.80 | 13.30 | 13.90 | 13.00 |
| | S.E. | 1.56 | 3.27 | 2.24 | 2.35 | 2.34 | 3.30 | 3.74 |
| 3 | Left eye | 22 | 16 | 12 | 0 | 0 | 0 | 0 |
| | Right eye | 28 | 26 | 16 | 18 | 18 | 14 | 0 |
| | Left eye | 24 | 24 | 18 | 4 | 4 | 4 | 4 |
| | Right eye | 22 | 14 | 12 | 12 | 0 | 0 | 0 |
| | Left eye | 20 | 18 | 16 | 16 | 14 | 4 | 4 |
| | Right eye | 24 | 13 | 9 | 4 | 4 | 2 | 0 |
| | Left eye | 22 | 20 | 20 | 18 | 14 | 12 | 2 |
| | Right eye | 17 | 9 | 2 | 0 | 0 | 0 | 0 |
| | Left eye | 20 | 16 | 16 | 16 | 14 | 12 | 7 |
| | Right eye | 20 | 11 | 7 | 2 | 0 | 0 | 0 |
| | Mean | 21.90 | 16.70 | 12.80 | 9.00 | 6.80 | 4.80 | 1.70 |
| | S.E. | 0.95 | 1.72 | 1.75 | 2.43 | 2.31 | 1.79 | 0.79 |

TABLE 15

| Group | Region | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| 4 | Right eye | 20 | 2 | 2 | 0 | 0 | 0 | 0 |
| | Left eye | 27 | 35 | 33 | 31 | 16 | 12 | 12 |
| | Right eye | 26 | 18 | 20 | 18 | 16 | 14 | 0 |
| | Left eye | 24 | 24 | 20 | 13 | 4 | 0 | 0 |
| | Right eye | 22 | 16 | 16 | 14 | 14 | 14 | 14 |
| | Left eye | 16 | 2 | 2 | 0 | 0 | 0 | 0 |
| | Right eye | 24 | 18 | 16 | 12 | 12 | 0 | 0 |
| | Left eye | 22 | 12 | 12 | 2 | 0 | 0 | 0 |

TABLE 15-continued

| Group | Region | Day 1 after inoculation | Day 2 after inoculation | Day 3 after inoculation | Day 4 after inoculation | Day 5 after inoculation | Day 6 after inoculation | Day 7 after inoculation |
|---|---|---|---|---|---|---|---|---|
| | Right eye | 24 | 6 | 4 | 4 | 0 | 0 | 0 |
| | Left eye | 10 | 0 | 0 | 0 | 0 | 0 | 0 |
| | Mean | 21.50 | 13.30 | 12.50 | 9.40 | 6.20 | 4.00 | 2.60 |
| | S.E. | 1.61 | 3.53 | 3.34 | 3.22 | 2.32 | 2.04 | 1.74 |
| 5 | Left eye | 16 | 2 | 2 | 0 | 0 | 0 | 0 |
| | Right eye | 24 | 18 | 16 | 12 | 0 | 0 | 0 |
| | Left eye | 27 | 20 | 18 | 14 | 9 | 4 | 2 |
| | Right eye | 20 | 20 | 14 | 2 | 2 | 0 | 0 |
| | Left eye | 6 | 4 | 2 | 0 | 0 | 0 | 0 |
| | Right eye | 31 | 10 | 4 | 2 | 0 | 0 | 0 |
| | Left eye | 26 | 15 | 4 | 2 | 0 | 0 | 0 |
| | Right eye | 24 | 9 | 4 | 0 | 0 | 0 | 0 |
| | Left eye | 26 | 18 | 14 | 10 | 0 | 0 | 0 |
| | Right eye | 26 | 19 | 10 | 4 | 0 | 0 | 0 |
| | Mean | 22.60 | 13.50 | 8.80 | 4.60 | 1.10 | 0.40 | 0.20 |
| | S.E. | 2.25 | 2.14 | 1.98 | 1.69 | 0.90 | 0.40 | 0.20 |

FIGS. 6 and 7 revealed that the equivalent anti-inflammatory effects can be achieved even when the initial eye drop administration started at a delayed time (comparison between Group 3 and Group 4 in FIG. 7). It is also verified that an increased number of eye drop administration can provide much enhanced anti-inflammatory effects (comparison between Group 4 and Group 5 in FIG. 7).

The invention claimed is:

1. An aqueous suspension formulation comprising:
   nanoparticles consisting essentially of a macrolide antibiotic; and
   a dispersion stabilizer comprising polyoxyethylene hydrogenated castor oil,
   wherein the nanoparticles have an average particle diameter of 500 nm or less and a 90% diameter of 1500 nm or less.

2. The aqueous suspension formulation of claim 1, wherein the nanoparticles are produced by mixing the macrolide antibiotic, a physiologically acceptable salt and/or a physiologically acceptable saccharide, a physiologically acceptable polyol and/or water, and the dispersion stabilizer.

3. The aqueous suspension formulation of claim 1, wherein the macrolide antibiotic is erythromycin, clarithromycin, roxithromycin, azithromycin, josamycin, rokitamycin, or kitasamycin.

4. The aqueous suspension formulation of claim 1, wherein the dispersion stabilizer further comprises a surfactant, an aggregation inhibitor, or a viscosity modifier.

5. The aqueous suspension formulation of claim 4, wherein the surfactant is polysorbate 80, polyethylene glycol monostearate, and/or polyoxyethylene polyoxypropylene glycol.

6. The aqueous suspension formulation of claim 4, wherein the aggregation inhibitor is polyvinyl alcohol, polyethylene glycol, lecithin, and/or polyvinylpyrrolidone.

7. The aqueous suspension formulation of claim 4, wherein the viscosity modifier is methyl cellulose, hydroxypropyl methyl cellulose, and/or hydroxyethyl cellulose.

8. The aqueous suspension formulation of claim 1, which has a low irritability.

9. A pharmaceutical composition comprising the aqueous suspension formulation of claim 1.

10. A kit containing nanoparticles consisting essentially of a macrolide antibiotic for preparing a pharmaceutical composition comprising the nanoparticles of a macrolide antibiotic, wherein the nanoparticles have an average particle diameter of 500 nm or less and a 90% diameter of 1500 nm or less, and wherein the kit further contains a dispersion stabilizer comprising polyoxyethylene hydrogenated castor oil.

11. A method for treating or preventing an inflammatory disease or an infectious disease in a subject in need thereof, comprising administering the aqueous suspension formulation of claim 1 to the subject.

12. The method of claim 11, wherein the aqueous suspension formulation is administered parenterally.

13. The method of claim 12, wherein the aqueous suspension formulation is administered topically or by injection.

14. The method of claim 13, wherein the aqueous suspension formulation is topically administered to eye, ear, nose, or lung.

15. The method of claim 14, wherein the aqueous suspension formulation is administered in the form of an eye drop, an ear drop, a nose drop, or an inhaler.

16. The method of claim of claim 11, wherein the inflammatory disease or the infectious disease is systemic.

17. The method of claim 11, wherein the inflammatory disease or the infectious disease is an inflammatory disease or an infectious disease of eye, ear, nose, and lung.

18. The aqueous suspension formulation of claim 1, wherein the macrolide antibiotic is clarithromycin, roxithromycin, azithromycin, josamycin, rokitamycin, or kitasamycin.

19. The aqueous suspension formulation of claim 1, wherein the macrolide antibiotic is clarithromycin.

* * * * *